(12) United States Patent
Olivier

(10) Patent No.: US 9,120,585 B2
(45) Date of Patent: Sep. 1, 2015

(54) DEVICE FOR THE TRANSFER OF A MEDIUM

(71) Applicant: EMD Millipore Corporation, Billerica, MA (US)

(72) Inventor: Stephane Olivier, Rosheim (FR)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 14/684,510

(22) Filed: Apr. 13, 2015

(65) Prior Publication Data

US 2015/0217882 A1 Aug. 6, 2015

Related U.S. Application Data

(62) Division of application No. 12/638,242, filed on Dec. 15, 2009, now Pat. No. 9,028,779.

(30) Foreign Application Priority Data

Dec. 18, 2008 (FR) ...................................... 08 58804

(51) Int. Cl.
*B01L 99/00* (2010.01)
*B65B 3/26* (2006.01)

(52) U.S. Cl.
CPC .......................................... *B65B 3/26* (2013.01)

(58) Field of Classification Search
CPC .................................. B01L 99/00; B65B 3/26
See application file for complete search history.

(56) References Cited

U.S. PATENT DOCUMENTS

| 214,367 | A | 4/1879 | Colvin |
| 229,695 | A | 7/1880 | Granger |
| 988,378 | A | 4/1911 | Olson |
| 1,503,132 | A | 7/1924 | Prator |

(Continued)

FOREIGN PATENT DOCUMENTS

| CN | 101022875 A | 8/2007 |
| DE | 2161702 | 6/1973 |

(Continued)

OTHER PUBLICATIONS

Millipore's Initial Infringement Contentions, Document No. 19, filed Oct. 8, 2009 in the United States District Court for the District of Massachusetts, Civil Action No. 09-10765 DPW, 16 pages.

(Continued)

*Primary Examiner* — Jyoti Nagpaul
(74) *Attorney, Agent, or Firm* — Nields, Lemack & Frame, LLC

(57) ABSTRACT

The device for the transfer of a medium comprises a magazine (2) and at least one transfer element (3) for transfer of said medium, said transfer element (3) comprising a duct (45) for transfer of said medium provided at one end with a needle (31), a septum (32), and a maneuvering unit (33) of said needle (31), said transfer element (3) also comprising means for locking (61, 65) adapted to cooperate with complementary locking means (15) of said magazine (2) to lock said needle (31) in a waiting position, said locking means (61, 62, 65) belonging to said maneuvering unit (33) and cooperating with said complementary locking means (15) at a location of said magazine (2) distinct from the location through which said duct (45) issues from the cavity (20), at the opposite end from the needle (31).

7 Claims, 10 Drawing Sheets

(56) References Cited

U.S. PATENT DOCUMENTS

| | | |
|---|---|---|
| 1,585,163 A | 5/1926 | Milner |
| 1,831,457 A | 11/1931 | Larsen |
| 1,852,445 A | 4/1932 | Calkins et al. |
| 2,012,836 A | 8/1935 | Talbot et al. |
| 2,122,991 A | 7/1938 | Polston |
| 2,240,888 A | 5/1941 | Hageline |
| 2,426,808 A | 9/1947 | Auer |
| 2,642,256 A | 6/1953 | Stehlin |
| 2,712,881 A | 7/1955 | Mathisen |
| 2,736,201 A | 2/1956 | Ohlsen et al. |
| 2,767,587 A | 10/1956 | Perkins |
| 2,776,473 A | 1/1957 | Dailey et al. |
| 2,779,350 A | 1/1957 | Owens |
| 2,844,964 A | 7/1958 | Guibert |
| 2,859,932 A | 11/1958 | Mackal |
| 2,865,394 A | 12/1958 | Presley |
| 2,872,817 A | 2/1959 | Pitts |
| 2,952,269 A | 9/1960 | Stehlin |
| 2,994,224 A | 8/1961 | Brown |
| 3,038,485 A | 6/1962 | Hosek |
| 3,039,482 A | 6/1962 | Goldberg |
| 3,097,532 A | 7/1963 | Brown et al. |
| 3,219,047 A | 11/1965 | Kircher, III et al. |
| 3,223,100 A | 12/1965 | Koenig et al. |
| 3,244,376 A | 4/1966 | Thompson |
| 3,260,120 A | 7/1966 | Stilwell |
| 3,276,447 A | 10/1966 | Hamilton et al. |
| 3,319,622 A | 5/1967 | Shiner |
| 3,390,677 A | 7/1968 | Razimbaud |
| 3,424,181 A | 1/1969 | Morse |
| 3,479,880 A | 11/1969 | Mutter et al. |
| 3,525,350 A | 8/1970 | Hosek |
| 3,621,719 A | 11/1971 | Goodman et al. |
| 3,633,621 A | 1/1972 | Myers |
| 3,638,499 A | 2/1972 | Saint-Andre |
| 3,678,959 A | 7/1972 | Liposky |
| 3,696,932 A | 10/1972 | Rosenberg |
| 3,736,099 A | 5/1973 | Begg et al. |
| 3,747,411 A | 7/1973 | McDermott et al. |
| 3,776,042 A | 12/1973 | Werra et al. |
| 3,779,082 A | 12/1973 | Galloway |
| 3,802,782 A | 4/1974 | Natelson |
| 3,848,581 A | 11/1974 | Cinqualbre et al. |
| 3,858,449 A | 1/1975 | Singer |
| 3,921,456 A | 11/1975 | Newcomb, Jr. et al. |
| 3,985,332 A | 10/1976 | Walker |
| 4,015,631 A | 4/1977 | Hayes |
| 4,018,059 A | 4/1977 | Hatch |
| 4,034,775 A | 7/1977 | Slagel |
| 4,055,179 A | 10/1977 | Manschot et al. |
| 4,061,709 A | 12/1977 | Miller et al. |
| 4,064,003 A | 12/1977 | Newton |
| 4,094,197 A | 6/1978 | Harris, Sr. et al. |
| 4,207,922 A | 6/1980 | Andrieux et al. |
| 4,244,224 A | 1/1981 | Conn |
| 4,294,247 A | 10/1981 | Carter et al. |
| 4,296,759 A | 10/1981 | Joslin et al. |
| 4,325,401 A | 4/1982 | Ukai et al. |
| 4,346,609 A | 8/1982 | Diesel |
| 4,353,386 A | 10/1982 | Slagel |
| 4,378,824 A | 4/1983 | Carder, Sr. |
| 4,423,641 A | 1/1984 | Ottung |
| 4,423,642 A | 1/1984 | Kuboichi |
| 4,454,772 A | 6/1984 | Brunner et al. |
| 4,458,543 A | 7/1984 | Mieth |
| 4,479,393 A | 10/1984 | Shores |
| 4,525,127 A | 6/1985 | Welker |
| 4,527,436 A | 7/1985 | Jones |
| 4,537,593 A | 8/1985 | Alchas |
| 4,557,151 A | 12/1985 | Welker |
| 4,569,236 A | 2/1986 | Kitchen et al. |
| 4,580,452 A | 4/1986 | Masson |
| 4,584,887 A | 4/1986 | Galen |
| 4,587,856 A | 5/1986 | Otis |
| 4,587,887 A | 5/1986 | Shibayama et al. |
| 4,622,457 A | 11/1986 | Bradley et al. |
| 4,630,847 A | 12/1986 | Blenkush |
| 4,657,027 A | 4/1987 | Paulsen |
| 4,669,312 A | 6/1987 | Maurer |
| 4,669,321 A | 6/1987 | Meyer |
| 4,704,910 A | 11/1987 | Conrad |
| 4,826,055 A | 5/1989 | Stull |
| 4,836,236 A | 6/1989 | Ladisch |
| 4,838,877 A | 6/1989 | Massau |
| 4,861,239 A | 8/1989 | Simmons et al. |
| 4,889,692 A | 12/1989 | Holtzman |
| 4,913,185 A | 4/1990 | Mattei |
| 4,941,517 A | 7/1990 | Galloway |
| 4,942,901 A | 7/1990 | Vescovini |
| 4,944,875 A | 7/1990 | Gaignet |
| 4,997,108 A | 3/1991 | Hata |
| 5,058,619 A | 10/1991 | Zheng |
| 5,095,765 A | 3/1992 | Filbey et al. |
| 5,117,872 A | 6/1992 | Yie |
| 5,158,558 A | 10/1992 | Melker et al. |
| 5,161,417 A | 11/1992 | Strong et al. |
| 5,177,872 A | 1/1993 | Lewis et al. |
| 5,246,204 A | 9/1993 | Ottung |
| 5,285,999 A | 2/1994 | Scholz |
| 5,296,197 A | 3/1994 | Newberg et al. |
| 5,360,413 A | 11/1994 | Leason et al. |
| 5,375,477 A | 12/1994 | Neill et al. |
| 5,398,557 A | 3/1995 | Shimizu et al. |
| 5,435,339 A | 7/1995 | Hayes |
| 5,452,746 A | 9/1995 | Hoobyar et al. |
| 5,463,908 A | 11/1995 | Rosolia |
| 5,468,388 A | 11/1995 | Goddard et al. |
| 5,474,546 A | 12/1995 | Ambrisco et al. |
| D366,935 S | 2/1996 | Arthun et al. |
| 5,520,218 A | 5/1996 | Hlavinka et al. |
| 5,525,301 A | 6/1996 | Newberg et al. |
| 5,533,983 A | 7/1996 | Haining |
| 5,535,635 A | 7/1996 | Shaw |
| 5,542,305 A | 8/1996 | Hollinger |
| 5,549,568 A | 8/1996 | Shields |
| 5,585,576 A | 12/1996 | Jaeger |
| D381,067 S | 7/1997 | Karmalm |
| 5,730,418 A | 3/1998 | Feith et al. |
| 5,747,708 A | 5/1998 | Weiberth |
| 5,755,155 A | 5/1998 | Buesing |
| 5,766,462 A | 6/1998 | Jones |
| 5,786,209 A | 7/1998 | Newberg et al. |
| 5,820,614 A | 10/1998 | Erskine et al. |
| 5,829,425 A | 11/1998 | Woods et al. |
| 5,868,433 A | 2/1999 | Matkovich |
| 5,885,255 A | 3/1999 | Jaeger, Jr. et al. |
| 5,897,526 A | 4/1999 | Vaillancourt |
| 5,911,252 A | 6/1999 | Cassel |
| 5,948,998 A | 9/1999 | Witte et al. |
| 6,009,684 A | 1/2000 | Buesing |
| 6,030,578 A | 2/2000 | McDonald |
| 6,032,543 A | 3/2000 | Arthun et al. |
| 6,068,617 A | 5/2000 | Richmond |
| 6,096,011 A | 8/2000 | Trombley, III et al. |
| 6,133,022 A | 10/2000 | Newberg et al. |
| 6,145,810 A | 11/2000 | Connolly et al. |
| 6,156,025 A | 12/2000 | Niedospial, Jr. et al. |
| 6,162,206 A | 12/2000 | Bindokas et al. |
| 6,170,800 B1 | 1/2001 | Meloul et al. |
| 6,196,522 B1 | 3/2001 | Yuen et al. |
| 6,210,372 B1 | 4/2001 | Tessmann et al. |
| 6,221,041 B1 | 4/2001 | Russo |
| 6,237,639 B1 | 5/2001 | Jougla et al. |
| 6,254,773 B1 | 7/2001 | Biltoft |
| 6,273,869 B1 | 8/2001 | Vaillancourt |
| 6,306,191 B1 | 10/2001 | McInerney et al. |
| 6,314,987 B1 | 11/2001 | Hay |
| 6,345,640 B1 | 2/2002 | Newberg et al. |
| 6,345,645 B1 | 2/2002 | Kenna et al. |
| D454,173 S | 3/2002 | Almasian et al. |
| 6,354,466 B1 | 3/2002 | Karpisek |
| 6,357,306 B1 | 3/2002 | Jaeger |
| 6,360,794 B1 | 3/2002 | Turner |
| 6,386,137 B1 | 5/2002 | Riche |

(56) References Cited

U.S. PATENT DOCUMENTS

| | | |
|---|---|---|
| 6,390,127 B2 | 5/2002 | Schick |
| 6,477,906 B1 | 11/2002 | Peterson |
| 6,516,677 B1 | 2/2003 | Suter |
| 6,558,365 B2 | 5/2003 | Zinger et al. |
| 6,568,844 B1 | 5/2003 | Arthun et al. |
| 6,601,823 B2 | 8/2003 | Newberg |
| 6,623,631 B1 | 9/2003 | Graus et al. |
| 6,648,006 B1 | 11/2003 | Ostergaard |
| 6,672,561 B2 | 1/2004 | Kerg et al. |
| 6,699,229 B2 | 3/2004 | Zinger et al. |
| 6,715,624 B2 | 4/2004 | Brockwell |
| 6,779,575 B1 | 8/2004 | Arthun |
| 6,860,162 B1 | 3/2005 | Jaeger |
| 6,871,669 B2 | 3/2005 | Meyer et al. |
| 6,902,144 B2 | 6/2005 | de Cler |
| 6,916,012 B2 | 7/2005 | Newberg |
| 7,137,974 B2 | 11/2006 | Almasian et al. |
| 7,195,181 B2 | 3/2007 | Steingass et al. |
| 7,195,182 B2 | 3/2007 | Fischer et al. |
| 7,272,981 B2 | 9/2007 | Bigalke |
| 7,273,550 B2 | 9/2007 | Gutman et al. |
| 7,293,475 B2 | 11/2007 | Furey et al. |
| 7,293,477 B2 | 11/2007 | Furey et al. |
| 7,350,535 B2 | 4/2008 | Liepold et al. |
| 7,473,360 B2 | 1/2009 | Hoffman et al. |
| 7,488,446 B2 | 2/2009 | Meyer et al. |
| 7,578,205 B2 | 8/2009 | Belongia |
| 7,578,936 B2 | 8/2009 | Gaignet et al. |
| 7,597,683 B2 | 10/2009 | Myhrberg et al. |
| RE41,169 E | 3/2010 | Arthun |
| 7,722,733 B2 | 5/2010 | Tomasetti et al. |
| 7,753,340 B2 | 7/2010 | Liepold et al. |
| 7,815,362 B2 | 10/2010 | Myhrberg et al. |
| 7,921,740 B2 | 4/2011 | Furey et al. |
| 7,927,316 B2 | 4/2011 | Proulx et al. |
| 7,959,754 B2 | 6/2011 | Arthun |
| 8,029,023 B2 | 10/2011 | Arthun et al. |
| 8,167,480 B2 | 5/2012 | Myhrberg et al. |
| 8,281,961 B2 | 10/2012 | Martin |
| 8,517,998 B2 | 8/2013 | Proulx et al. |
| 8,539,988 B2 | 9/2013 | Guedon |
| 8,544,497 B2 | 10/2013 | Hillier et al. |
| 8,549,935 B2 | 10/2013 | Furey et al. |
| 8,562,572 B2 | 10/2013 | Proulx et al. |
| 8,579,871 B2 | 11/2013 | Proulx et al. |
| 8,646,342 B2 | 2/2014 | Furey et al. |
| 8,690,120 B2 | 4/2014 | Hartnett et al. |
| 8,915,264 B2 | 12/2014 | Hillier et al. |
| 8,919,365 B2 | 12/2014 | Hillier et al. |
| 9,028,779 B2 | 5/2015 | Olivier |
| 2002/0129858 A1 | 9/2002 | Meyer et al. |
| 2003/0188588 A1 | 10/2003 | Jaeger |
| 2005/0016620 A1 | 1/2005 | Proulx et al. |
| 2005/0035597 A1 | 2/2005 | Bamberger et al. |
| 2005/0090797 A1 | 4/2005 | Almasian et al. |
| 2005/0132821 A1 | 6/2005 | Furey et al. |
| 2005/0150546 A1 | 7/2005 | Liepold et al. |
| 2005/0285066 A1 | 12/2005 | Huang |
| 2006/0081804 A1 | 4/2006 | Cong |
| 2006/0086922 A1 | 4/2006 | Jensen et al. |
| 2006/0091060 A1 | 5/2006 | Gutman et al. |
| 2006/0142730 A1 | 6/2006 | Proulx et al. |
| 2006/0201263 A1 | 9/2006 | Furey et al. |
| 2006/0211995 A1 | 9/2006 | Myhrberg et al. |
| 2006/0243942 A1 | 11/2006 | Liepold et al. |
| 2006/0272432 A1 | 12/2006 | Belongia |
| 2007/0106264 A1 | 5/2007 | Proulx et al. |
| 2007/0193375 A1 | 8/2007 | Pandori et al. |
| 2007/0253287 A1 | 11/2007 | Myhrberg et al. |
| 2008/0000820 A1 | 1/2008 | Mitchell |
| 2008/0022785 A1 | 1/2008 | Furey et al. |
| 2008/0087860 A1 | 4/2008 | Vaillancourt et al. |
| 2008/0103476 A1 | 5/2008 | Schulte |
| 2008/0185552 A1 | 8/2008 | Myhrberg et al. |
| 2008/0277878 A1 | 11/2008 | Arthun et al. |
| 2009/0019952 A1 | 1/2009 | Furey et al. |
| 2009/0054758 A1 | 2/2009 | Dunseath |
| 2009/0101575 A1 | 4/2009 | Alburty et al. |
| 2009/0229671 A1 | 9/2009 | Hartnett et al. |
| 2009/0250157 A1 | 10/2009 | Arthun |
| 2010/0123094 A1 | 5/2010 | Zumbrum |
| 2010/0133459 A1 | 6/2010 | Zumbrum |
| 2010/0154569 A1 | 6/2010 | Guedon |
| 2010/0158759 A1 | 6/2010 | Olivier |
| 2010/0290311 A1 | 11/2010 | Myhrberg et al. |
| 2010/0326212 A1 | 12/2010 | Furey et al. |
| 2011/0155258 A1 | 6/2011 | Zumbrum |
| 2011/0155274 A1 | 6/2011 | Zumbrum |
| 2011/0197989 A1 | 8/2011 | Proulx et al. |
| 2011/0250626 A1 | 10/2011 | Williams et al. |
| 2011/0253233 A1 | 10/2011 | Hillier et al. |
| 2013/0199639 A1 | 8/2013 | Hartnett et al. |
| 2013/0306897 A1 | 11/2013 | Hillier et al. |
| 2013/0312492 A1 | 11/2013 | Hillier et al. |
| 2013/0334450 A1 | 12/2013 | Proulx et al. |
| 2014/0000753 A1 | 1/2014 | Guedon |
| 2014/0014230 A1 | 1/2014 | Guedon |
| 2014/0014231 A1 | 1/2014 | Guedon |
| 2014/0026989 A1 | 1/2014 | Hillier et al. |

FOREIGN PATENT DOCUMENTS

| | | |
|---|---|---|
| DE | 32 15799 A1 | 11/1983 |
| DE | 3 633 431 A1 | 4/1988 |
| DE | 3 701 250 A1 | 7/1988 |
| DE | 8812723 U1 | 12/1988 |
| DE | 100 39 196 A1 | 2/2002 |
| DE | 69807924 T2 | 1/2003 |
| DE | 603 10 700 T2 | 10/2007 |
| EP | 0 103 396 A2 | 3/1984 |
| EP | 0107579 A2 | 5/1984 |
| EP | 0154002 A1 | 9/1985 |
| EP | 0 510 355 A1 | 10/1992 |
| EP | 0508749 A2 | 10/1992 |
| EP | 0 576 380 A1 | 12/1993 |
| EP | 0 468 957 B1 | 6/1994 |
| EP | 0 684 050 A2 | 11/1995 |
| EP | 0691492 A1 | 1/1996 |
| EP | 1008359 A1 | 6/2000 |
| EP | 1 231 699 A1 | 8/2002 |
| EP | 1321699 A2 | 6/2003 |
| EP | 1329210 A1 | 7/2003 |
| EP | 1548420 A2 | 6/2005 |
| EP | 1 370 788 B1 | 11/2005 |
| EP | 0858589 B1 | 12/2005 |
| EP | 1 499 382 B1 | 12/2006 |
| EP | 1 962 076 A2 | 8/2008 |
| FR | 2023259 A1 | 8/1970 |
| GB | 943132 | 11/1963 |
| GB | 1381391 | 1/1975 |
| GB | 1418046 | 12/1975 |
| GB | 1463303 | 2/1977 |
| GB | 1479226 | 7/1977 |
| GB | 1511240 | 5/1978 |
| GB | 1573482 | 8/1980 |
| GB | 2 327 369 A | 1/1999 |
| GB | 2365511 A | 2/2002 |
| JP | 42-15498 U | 9/1967 |
| JP | 44-4942 U | 2/1969 |
| JP | 45-3461 B | 2/1970 |
| JP | 49-112631 | 9/1974 |
| JP | 58-131802 U | 9/1983 |
| JP | 59-38278 | 3/1984 |
| JP | 2-052667 A | 2/1990 |
| JP | 2-71728 A | 3/1990 |
| JP | 02-118276 A | 5/1990 |
| JP | 2-121679 U | 10/1990 |
| JP | 03-141948 A | 6/1991 |
| JP | 6-010845 U | 2/1994 |
| JP | 6-023045 A | 2/1994 |
| JP | 6-78669 U | 11/1994 |
| JP | 06-327772 A | 11/1994 |
| JP | 07-051371 A | 2/1995 |
| JP | 8-502339 A | 3/1996 |

(56) References Cited

FOREIGN PATENT DOCUMENTS

| | | |
|---|---|---|
| JP | 08-168535 A | 7/1996 |
| JP | 9-133248 A | 5/1997 |
| JP | 9-154945 A | 6/1997 |
| JP | 9-313896 A | 12/1997 |
| JP | 9-512892 A | 12/1997 |
| JP | 11-141713 A | 5/1999 |
| JP | 11-270705 A | 10/1999 |
| JP | 11-514741 A | 12/1999 |
| JP | 2000-055792 A | 2/2000 |
| JP | 2001-170188 A | 6/2001 |
| JP | 2001-510088 A | 7/2001 |
| JP | 2001-269401 A | 10/2001 |
| JP | 2001-523525 A | 11/2001 |
| JP | 2002-510996 A | 4/2002 |
| JP | 2003-181248 A | 7/2003 |
| JP | 2004-332797 A | 11/2004 |
| JP | 2005-181336 A | 7/2005 |
| JP | 2005-519825 A | 7/2005 |
| JP | 2006-516723 A | 7/2006 |
| JP | 2008-185218 A | 8/2008 |
| JP | 2009-2965 A | 1/2009 |
| JP | 2009-192540 A | 8/2009 |
| JP | 4332106 B2 | 9/2009 |
| SU | 649954 | 2/1979 |
| WO | 86/02450 A1 | 4/1986 |
| WO | 90/12972 A1 | 11/1990 |
| WO | 91/00215 A1 | 1/1991 |
| WO | 94/08173 A1 | 4/1994 |
| WO | 94/19086 A1 | 9/1994 |
| WO | 95/30856 A1 | 11/1995 |
| WO | 96/30076 A1 | 10/1996 |
| WO | 97/16715 A1 | 5/1997 |
| WO | 98/45188 A1 | 10/1998 |
| WO | 98/50105 A1 | 11/1998 |
| WO | 99/03568 A1 | 1/1999 |
| WO | 99/06089 A1 | 2/1999 |
| WO | 99/26580 A1 | 6/1999 |
| WO | 00/78472 A1 | 12/2000 |
| WO | 03/090842 A1 | 11/2003 |
| WO | 03/090843 A1 | 11/2003 |
| WO | 2005/012775 A1 | 2/2005 |
| WO | 2006/022816 A2 | 3/2006 |
| WO | 2006/026253 A2 | 3/2006 |
| WO | 2008/042285 A2 | 4/2008 |
| WO | 2008/048511 A2 | 4/2008 |
| WO | 2008/136720 A1 | 11/2008 |
| WO | 2010/008395 A1 | 1/2010 |
| WO | 2010/008396 A2 | 1/2010 |
| WO | 2010/122081 A1 | 10/2010 |
| WO | 2012/114105 A1 | 8/2012 |
| WO | 2013/011231 A1 | 1/2013 |

OTHER PUBLICATIONS

Gore's Preliminary Non-Infringement Contentions to Plaintiff Millipore Corporation, Document No. 20, filed Oct. 29, 2009 in the United States District Court for the District of Massachusetts, Civil Action No. 09-10765 DPW, 30 pages.
Gore's Preliminary Invalidity Contentions to Plantiff Millipore Corporation, Document No. 21, filed Oct. 29, 2009 in the United States District Court for the District of Massachusetts, Civil Action No. 09-10765 DPW, 108 pages.
Preliminary Noninfringement and Invalidity Disclosures of Allpure Technologies, Inc., Document 22, filed Jul. 20, 2011 in the United States District Court for the District of Massachusetts, Civil Action No. 11-cv-10221-DPW, 15 pages.
Gore's First Supplemental Response to Millipore's First Set of Interrogatories [Interrogatory Nos. 11, 15 and 16] dated Nov. 1, 2011, United States District Court for the District of Delaware, Civil Action No. 11-346-SLR, 86 pages.
Gore's Third Supplemental Response to Millipore's First Set of Interrogatories [Interrogatory No. 11], Civil Action No. 11-346-SLR, United States District Court for the District of Delaware, dated Dec. 21, 2011, part 1—pp. 1-43; part 2—pp. 44-85 with Exhibits A-E (334 pages), Exhibits F-G (115 pages) and Exhibits H-I (114 pages). (Note due to the size limitations this is uploaded into 5 parts).
Gore's Fourth Supplemental Response to Millipore's First Set of Interrogatories [Interrogatories Nos. 11 and 12], Civil Action No. 11-346-SLR in the USDC for the District of Delaware, dated May 9, 2012, 172 pages.
Memorandum and Order, Document No. 70, dated Sep. 20, 2010, in the United States District Court for the District of Massachusetts, Civil Action No. 09-10765-DPW, 59 pages.
Correspondence from T. Pender to C. Burrell dated Dec. 2, 2011 regarding C.A. No. 11-CV-346-SLR (Bates Stamp GF000001-GF000008), 8 pages.
Documents Produced by Third Party Casella Sales and Marketing Inc., Bates No. CSMI000001 through CSMI000066, 65 pages, Nov. 2011.
Allegheny Bradford Corporation's Objections and Responses to Subpoena, Civil Action No. 1:11-cv-00346-SLR, dated Dec. 15, 2011 in the USDC for the District of Delaware, and Bates # ABC00001 through Bates # ABC000012, 19 pages.
Fluid Line Technology Corporation Documents produced in *Gore* v. *Millipore*, Nov. 28, 2011, Bates # FLT000001 through Bates # FLT000103, 48 pages.
File history of U.S. Appl. No. 78/140,217, filed Jul. 1, 2002, 53 pages.
About Fluid Line Technology, http://www/fluidlinetech.com/aboutus.html, dated May 8, 2012 and Oct. 30, 2009, 35 pages.
Allegro Single-use Systems—Recommended Capsule Filters and Membranes, http://www.pall.com/main/Biopharmaceuticals/Product.page?id-48022 and http://www.pall.com/variants/print/biopharm_48022.asp, dated May 8, 2012 and Oct. 30, 2009, 51 pages.
Tingley, S., "Plastic factory: Disposable biopharmaceutical manufacturing takes a giant leap forward", Alternative Manufacturing, Clean Rooms, pp. S4-S9, (Feb. 2003), 6 pages.
Tingley, S., "Plastic factory, Part II: The final pieces of the disposable puzzle", Alternative Manufacturing, Clean Rooms, pp. 12-14 (Jun. 2003), 4 pages.
Wendt, D., "BioTrends: Disposable Processing Systems: How Suppliers Are Meeting Today's Biotech Challenges from Fluid Handling to Filtration", Biopharm International, p. 18 (Jul. 2003), 7 pages.
Haughney, H. and H. Aranha, "Disposable Processing Gains you a Competitive Edge: Enhancing Manufacturing Capacity with Disposable Filters, Connectors, and Membrane Chromatagraphy", Biopharm International, p. 50 (Oct. 2003), 7 pages.
Casella Sales & Marketing Inc., CSMI Sample Valves. Datasheet [online]. Retrieved from the Internet: www.casellasales.com (2 pages), product offered online as early as Aug. 2008, according to URL search performed on http://web.archive.org.
File history of U.S. Appl. No. 60/375,747, filed Apr. 26, 2002, Document 53-2, Case 1:09-cv-10765-DPW, filed May 25, 2010, 50 pages.
File history of U.S. Appl. No. 60/500,024, filed Sep. 4, 2003, 23 pages.
International Search Report for PCT/US03/12924, dated Aug. 6, 2003, 2 pages.
International Search Report for PCT/US03/12927 dated Aug. 6, 2003, 3 pages.
International Search Report for PCT/US03/13073 dated Aug. 6, 2003, 7 pages.
International Search Report on PCT/US2008/070482, date of mailing: Apr. 16, 2009, 2 pages.
Written Opinion of the International Searching Authority (Appln. No. PCT/US2008/070482, filed Jul. 18, 2008) mailed Apr. 16, 2009, 4 pages.
International Search Report on PCT/US2011/021341, date of mailing: Sep. 27, 2011, 4 pages.
International Preliminary Report on Patentability (Appln. No. PCT/US2008/070482, filed Jul. 18, 2008) mailed Jan. 27, 2011, pp. 1-6.
International Preliminary Report on Patentability (Appln. No. PCT/US2008/070488, filed Jul. 18, 2008) mailed Jan. 27, 2011, pp. 1-6.
European Search Report EP 1548420 A3, regarding EP App. No. 04029883, dated Mar. 13, 2006, 4 pages.
International Preliminary Examination Report for PCT/US03/12924 dated Jul. 8, 2004, 11 pages.

(56) References Cited

OTHER PUBLICATIONS

International Preliminary Examination Report for PCT/US03/12927 dated Feb. 11, 2004, 2 pages.
Notice of Allowance mailed Oct. 11, 2013 in co-pending U.S. Appl. No. 12/872,436.
Chinese Communication, with English translation, issued Dec. 4, 2013 in co-pending Chinese patent application No. 2010105313860.
Notice of Allowance mailed Dec. 24, 2013 in co-pending U.S. Appl. No. 12/291,814.
Japanese communication, with English translation, mailed Feb. 18, 2014 in co-pending Japanese patent application No. JP 2013-032622.
Notice of Allowance mailed May 22, 2014 in co-pending U.S. Appl. No. 13/955,309.
Office Action mailed Apr. 18, 2014 in co-pending U.S. Appl. No. 14/040,777.
Notice of Allowance mailed Jun. 4, 2014 in corresponding parent U.S. Appl. No. 12/638,242.
International Search Report and Written Opinion mailed Apr. 3, 2014 in PCT application No. PCT/US2013/075460.
Japanese communication, with English translation, mailed Jul. 1, 2014 in co-pending Japanese patent application No. JP 2013-161276.
Notice of Allowance mailed Jul. 9, 2014 in co-pending U.S. Appl. No. 13/955,309.
Miscellaneous Communication mailed Aug. 20, 2014 in co-pending U.S. Appl. No. 13/955,309.
Notice of Allowance mailed Aug. 11, 2014 in co-pending U.S. Appl. No. 13/956,428.
Corrected Notice of Allowability mailed Sep. 10, 2014 in co-pending U.S. Appl. No. 13/956,428.
Notice of Allowance mailed Jun. 30, 2014 in corresponding parent U.S. Appl. No. 12/638,242.
Supplemental Notice of Allowability mailed Aug. 21, 2014 in corresponding parent U.S. Appl. No. 12/638,242.
Notice of Allowance mailed Oct. 6, 2014 in co-pending U.S. Appl. No. 13/955,309.
Notice of Allowance mailed Sep. 30, 2014 in co-pending U.S. Appl. No. 13/956,428.
Office Action mailed Mar. 20, 2015 in co-pending U.S. Appl. No. 13/827,747.
Notice of Allowance mailed Feb. 25, 2015 in corresponding parent U.S. Appl. No. 12/638,242.
Office Action mailed May 20, 2015 in co-pending U.S. Appl. No. 14/012,103.
Notice of Allowance mailed Jun. 5, 2015 in co-pending U.S. Appl. No. 14/032,211.
Office Action mailed Jun. 17, 2015 in co-pending U.S. Appl. No. 14/032,358.
Greene, R., et al., "Disposable Equipment: A Mainstay in Bioprocessing", Chemical Engineering Progress, vol. 98, Issue 11, (Nov. 2002), 9 pages.
Haughney, H., et al., "Taking Disposable Processing to the Next Level", Clean Rooms, (Jun. 2004), 5 pages.
Colder Products—Quick Couplings & Fittings for Industrial Applications—Industrial Products, http://www.colder.com/Markets/Industrial/IndustrialProducts/tabid/821/Default.aspx?ProductId=22, dated Oct. 30, 2009, 17 pages.
Daily Business Briefing—"Entegris Introduces the First All Teflon PFA/Process Tee Valve", dated Apr. 16, 2002, 2 pages.
ESP Sanitary Sample Valves Operation and Maintenance Instructions dated Nov. 1995, (WLG-DEL00039664-WLG-DEL00039678), Millipore Corporation, 16 pages.
Sanitary Inline Bleed and Sample Valves. Datasheet [online], Fluid Line Technology, Retrieved from the Internet: www.fluidlinetech.com (1 page), document created on Mar. 2, 2009 according to document properties.
ITT Dualrange Control Valve. Data Sheet [online], Pure-Flo. Retrieved from the Internet: www.ittpureflo.com (2 pages), document created Jan. 12, 2007 according to document properties.

Block, S.S., Disinfection, Sterilization, and Preservation (Fourth Edition), Chapter 11, Alcohols, pp. 191-203, by Larson, et al., Lea & Febiger, ISBN:0-8121-1364-0, 1991 (only the year was cited on the publication), 15 pages.
Lynx ST Connectors http://www.millipore.com/catalogue/module/c9131 dated Oct. 30, 2009, 9 pages.
Lynx Trademark Reg. No. 2,831,931, first use Apr. 1, 2003, registered Apr. 13, 2004, 3 pages.
Microbiological Analysis (Sampling Equipment)—Sampling Ports, p. 130, 1989 (only the year is available for this publication).
NovAseptic—How to Use NA sampling system, http://www.novaseptic.se/main.asp?typ=6, dated Feb. 13, 2002, 2 pages.
NovAseptic, Novaseptum Liquid Sampling System—Totally Enclosed System/ No Cross Contamination/ Presterilized Disposable Unit/ Pyrogen Free, p. 1-4, Feb. 2003.
Opticap Valve: Millipore Application Note, Jul. 2000, "Gamma Compatible Sterilizing Grade Filter Capsules for Use with Disposable Manufacturing Containers"; 6-pages.
Opticap Vent; Millipore Data Sheet, Apr. 2005, "Gamma Compatible Sterilizing-grade Durapore 0.1 um and 0.22 um Filters", 8-pages.
Opticap3; Millipore Corporation, Nov. 2001, "Opticap TM Capsules with Millistak+™. Media User Guide", 4-pages.
Janetschek, R., "Capsule Filters & Disposable Sterile Processing Systems", Pharmaceutical Processing, vol. 18, No. 11, p. 8 (Jan. 2001), 4 pages.
"New quality of data for bioprocessing bags. (Application Area)." Pharmaceutical Processing, Jan. 2002, Charter Medical, Ltd., Bioprocess Products, Retrieved from the Internet on Feb. 16, 2010 from accessmylibrary: <URL: http://www.accessmylibrary.com/coms2/summary_0286-25022745_ITM>, pp. 1-2.
Pharmenta AptiPort Sampling Valve, http://www.web.archive.org/web/20031029084907/http://www.pharmenta.com/aptiport.htm, 1 page, last modified Mar. 29, 2004, retrieved from internet May 8, 2012.
Landon, R., et al., "Bridging the Gap: A case study in the validation of hybrid connectors", Process PharmaTEC International, issue Jun. 2004 (RP1007EN00), pp. 16-17, Nov. 2004, 3 pages.
ITT, Pure-Flo Hygienic diaphragm valves, actuators, and switch packages, http://www.ittpureflo.com/valvetype.html dated May 8, 2012 and Oct. 30, 2009, 12pages.
Pure-Flo: Sample and Bleed Valves for the pharmaceutical and bioprocessing industries, dated Sep. 1992, ITT Fluid Tech. Corp., (Bates stamp WLG=DEL00039389-WLG-DEL00039394), 6 pages.
Pure-Flo Solutions, Pure-Flo Radial Seated Tank Bottom Diaphragm Valve, Datasheet [online], ITT Industries, 2001 (only the year was cited on the publication), (2 pages).
Risk Free Connection of Sterilized Single-Use Fluid Path Assemblies to Stainless Steel SIP Systems with Lynx ST (Steam-To) Connectors [online], Millipore Corporation Application Note, Rev. A, Lit. No. AN7428EN00, May, 2008. Retrieved from the Internet: www.millipore.com (8 pages).
Sani-Tech Globe & Angle Valve product information, dated Aug. 1989, (Bates stamp WLG-DEL00040302-WLG-DEL00040304), 3 pages.
"Sip-Able Sample Valve," Datasheet [online]. Retrieved from the Internet: www.fluidlinetech.com (1 page), product offered online as early as Jun. 26, 2007, according to URL search performed on http://web.archive.org.
Steam-In-Place Bag Connector, http://www.fluidcomponents.net/tc_tech.html, download on Feb. 18, 2010, 1 page.
"Rapid Aseptic Fluid Transfer System Introduction" Stedim Biosystems. [online]. Retrieved from the Internet: <URL: http: www.stedim.com/p2A_IDC_introduction_php> (2 pages), dated Nov. 21, 2007.
Valves, Gemu Valves and Distributor, Diaphragm Valves, Sanitary Valves, Aseptic Valves, Valves and Fittings, Casella Sales and Marketing, Inc., http://www.casellasales.com, dated May 8, 2012 and Oct. 30, 2009, 13 pages.
Waukesha Cherry-Burrell Manual Valves, dated May 2000 (Bates stamp CSMI000044-CSMI000066), 23 pages.
Office Action dated Sep. 22, 2005 in U.S. Appl. No. 10/500,077.
Final Rejection dated Apr. 21, 2006 in U.S. Appl. No. 10/500,077.
Office Action dated Nov. 16, 2006 in U.S. Appl. No. 10/500,077.

(56) References Cited

OTHER PUBLICATIONS

Final Rejection dated Sep. 10, 2007 in U.S. Appl. No. 10/500,077.
Office Action dated Apr. 15, 2008 in U.S. Appl. No. 10/500,077.
Office Action dated Nov. 28, 2008 in U.S. Appl. No. 10/500,077.
Final Rejection dated Apr. 14, 2009 in U.S. Appl. No. 10/500,077.
Notice of Allowance dated Jan. 25, 2010 in U.S. Appl. No. 10/500,077.
Notice of Allowance dated Apr. 15, 2010 in U.S. Appl. No. 10/500,077.
Office Action dated Aug. 12, 2010 in U.S. Appl. No. 10/500,077.
Notice of Allowance dated Dec. 7, 2010 in U.S. Appl. No. 10/500,077.
Office Action dated Aug. 19, 2009 in U.S. Appl. No. 11/350,384.
Final Rejection dated May 12, 2010 in U.S. Appl. No. 11/350,384.
Office Action mailed Aug. 25, 2011 in U.S. Appl. No. 11/350,384.
Final Rejection mailed Mar. 5, 2012 in U.S. Appl. No. 11/350,384.
Office Action dated Mar. 16, 2010 in U.S. Appl. No. 11/584,301.
Fluid Line Technology Corporation, FLT Bleed/Sample Valve Maintenance, Nov. 10, 2008. Datasheet [online], Fluid Line Technology. Retrieved from the Internet: www.fluidlinetech.com (1 page).
ITT Sample & Bleed Valves. Datasheet [online], ITT Corporation, 2006. Retrieved from the Internet: www.ittpureflo.com (4 pages).
Guidelines for Using The Lynx ST Connector. Technical Brief [online], Millipore Corporation, 2008. Retrieved from the Internet: www/millipore.com (2 pages).
"Connecting the Sanitary Flange," Datasheet [online], Millipore Corporation, 2007 (pp. 1-2).
Final Rejection dated Oct. 7, 2010 in co-pending U.S. Appl. No. 11/584,301.
Office Action dated Jan. 30, 2009 in co-pending U.S. Appl. No. 11/878,126.
Final Rejection dated Jun. 26, 2009 in co-pending U.S. Appl. No. 11/878,126.
Office Action dated Aug. 12, 2009 in co-pending U.S. Appl. No. 11/878,126.
Office Action dated Sep. 25, 2009 in co-pending U.S. Appl. No. 11/878,126.
Final Rejection dated Apr. 6, 2010 in co-pending U.S. Appl. No. 11/878,126.
Notices of Allowance dated Feb. 16, 2011 in co-pending U.S. Appl. No. 11/878,126.
Notice of Allowance dated Mar. 1, 2011 in co-pending U.S. Appl. No. 11/878,126.
Office Action dated Mar. 19, 2010 in co-pending U.S. Appl. No. 12/284,666.
Notice of Allowance dated Oct. 1, 2010 in co-pending U.S. Appl. No. 12/284,666.
Supplemental Notice of Allowance dated Oct. 7, 2010 in co-pending U.S. Appl. No. 12/284,666.
Supplemental Notice of Allowance dated Oct. 15, 2010 in co-pending U.S. Appl. No. 12/284,666.
Supplemental Notice of Allowance dated Oct. 20, 2010 in co-pending U.S. Appl. No. 12/284,666.
Notice of Allowance mailed Mar. 29, 2012 in co-pending U.S. Appl. No. 12/284,666.
Office Action mailed Jun. 26, 2012 in co-pending U.S. Appl. No. 12/872,436.
Office Action mailed Aug. 29, 2012 in co-pending U.S. Appl. No. 12/902,430.
Office Action mailed Oct. 3, 2012 in co-pending U.S. Appl. No. 13/092,566.
Office Action mailed Nov. 30, 2012 in co-pending U.S. Appl. No. 12/284,666.
Final Rejection mailed Oct. 10, 2012 in co-pending U.S. Appl. No. 12/872,436.
Office Action mailed Dec. 21, 2012 in co-pending U.S. Appl. No. 12/638,283.
Office Action Dec. 8, 2011 in co-pending U.S. Appl. No. 12/291,814.
Final Rejection mailed Jun. 20, 2012 in co-pending U.S. Appl. No. 12/291,814.
Office Action mailed Oct. 5, 2012 in co-pending U.S. Appl. No. 12/291,814.
Notice of Allowance mailed Jul. 3, 2013 in co-pending U.S. Appl. No. 13/092,566.
Notice of Allowance mailed Jul. 5, 2013 in co-pending U.S. Appl. No. 11/584,301.
Notice of Allowance mailed Jul. 8, 2013 in co-pending U.S. Appl. No. 12/284,666.
Notice of Allowance mailed Jul. 16, 2013 in co-pending U.S. Appl. No. 12/902,430.
Notice of Allowance mailed Jul. 18, 2013 in co-pending U.S. Appl. No. 12/638,283.
Notice of Allowance mailed Aug. 2, 2013 in co-pending U.S. Appl. No. 11/350,384.
Entegris Impact Mini Disposable Filters, Product Information brochure, 4414-2646ENT-1006, 2006, 4 pages.
Millipore Corporation, Milli-Q Direct Water Purification System brochure, Lit. No. PB1032EN00, Jan. 2012, 8 pages.
Entegris Impact Asymmetric Disposable Filters, Product Information brochure, 4414-5723ENT-0511, 2006, 6 pages.
Millipore Corporation, Milli-Q Advantage A10 Water Purification Systems brochure, Lit. No. PB0001EN00, 2013, 12 pages.
Millipore Publication, NovAseptic, NovaSeptum Liquid Sampling System, dated Nov. 2001, P75185, Rev. B (Bates stamp—WLG-DEL00040809-WLG-DEL00040813), 6 pages.
Japanese Communication mailed Dec. 6, 2011 in corresponding Japanese Patent Application No. 2009-282419, 6 pages.
French Search Report mailed Nov. 13, 2009 in corresponding French Patent Application No. FR 0858804.
European Communication mailed Feb. 2, 2010 in corresponding European Patent Application No. 09290917.5, 5 pages.
French Search Report mailed Nov. 20, 2009 in co-pending French Patent Application No. FR 0858805.
European Communication mailed Jan. 29, 2010 in co-pending European Patent Application No. 09290918.3, 6 pages.
Extended European Search Report mailed Dec. 21, 2010 in co-pending European Patent Application No. 08253748.1.
European Communication dated Oct. 29, 2010 in a co-pending foreign application (EP10179151.5), 6 pages.
European Communication dated Oct. 29, 2010 in a co-pending foreign application (EP10179183.8), 6 pages.
Indian communication dated Oct. 18, 2010 in a co-pending foreign application (IN1444/DELNP/2004), 2 pages.
Notice of Rejection, with English Translation, dated Jul. 24, 2007 in co-pending Japanese Patent Application No. JP 2003-587467, 6 pages.
Japanese Communication dated Jul. 27, 2010 in a co-pending foreign application JP2008-070904, 3 pages.
Japanese Communication dated Dec. 1, 2010 in a co-pending foreign application JP2008-237495, 3 pages.
Japanese Communication dated Dec. 1, 2010 in a co-pending foreign application JP 2009-111794, 5 pages.
Japanese Communication, with English translation, dispatched Aug. 21, 2012 in co-pending Japanese patent application No. JP 2010-245357.
English translation of Chinese Communication issued Aug. 29, 2012 in co-pending Chinese patent application No. CN 201010531386.0.
Final Rejection mailed Sep. 12, 2013 in co-pending U.S. Appl. No. 12/872,436.
Japanese Communication, with English translation, mailed Feb. 5, 2013 in co-pending Japanese Patent Application No. JP 2011-179614.
Japanese Communication, with English translation, mailed Mar. 26, 2013 in co-pending Japanese Patent Application No. 2008-288424.
Notice of Allowance mailed Mar. 22, 2013 in co-pending U.S. Appl. No. 13/092,566.
Notice of Allowance mailed Apr. 8, 2013 in co-pending U.S. Appl. No. 12/902,430.
Notice of Allowance mailed Apr. 22, 2013 in co-pending U.S. Appl. No. 11/584,301.
Office Action mailed May 3, 2013 in co-pending U.S. Appl. No. 12/872,436.

(56) References Cited

OTHER PUBLICATIONS

Notice of Allowance mailed Jun. 3, 2013 in co-pending U.S. Appl. No. 12/638,283.
Memorandum and Order Denying Millipore's Motion to Alter Judgment and for Reconsideration, U S District Court for the District of Massachusetts, *EMD Millipore Corporation* v. *W. L. Gore & Associates, Inc.*, Civil Action No. 09-10765-DPW, Document 93, Dated Mar. 20, 2012, 16 pages.
Gore's Prior Art Statement with Exhibits A through I (entire document), U S District Court for the District of Delaware, *W. L. Gore & Associates, Inc.* v. *EMD Millipore Corporation*, Civil Action No. 11-346-SLR, Dated Dec. 21, 2011, 55 pages.
Millipore's List of Claim Terms to Be Construed and Proposed Constructions, U S District Court for the District of Delaware, *W. L. Gore & Associates, Inc.* v. *EMD Millipore Corporation*, Civil Action No. 11-346-SLR, Dated May 30, 2012, 8 pages.
Gore's List of Claim Terms and Proposed Constructions, U S District Court for the District of Delaware, *W. L. Gore & Associates, Inc.* v. *EMD Millipore Corporation*, Civil Action No. 11-346-SLR, Dated May 30, 2012, 4 pages.
Millipore's Responsive Constructions of Claim Terms, U S District Court for the District of Delaware, *W. L. Gore & Associates, Inc.* v. *EMD Millipore Corporation*, Civil Action No. 11-346-SLR, Dated Jun. 20, 2012, 5 pages.
Gore's List of Responsive Claim Constructions, U S District Court for the District of Delaware, *W. L. Gore & Associates, Inc.* v. *EMD Millipore Corporation*, Civil Action No. 11-346-SLR, Dated Jun. 27, 2012, 8 pages.
Gore's Motion for Leave to Amend Its Complaint for Declaratory Judgment, US District Court for the District of Delaware, *W. L. Gore & Associates, Inc.* v. *EMD Millipore Corporation*, Civil Action No. 11-346-SLR-MPT, Document 71, Dated Aug. 8, 2012, 3 pages.
Exhibits 1 and 2 to Gore's Motion for Leave to Amend Its Complaint for Declaratory Judgment, US District Court for the District of Delaware, *W. L. Gore & Associates, Inc.* v. *EMD Millipore Corporation*, Civil Action No. 11-346-SLR-MPT, Document 75, Redacted—Public Version, Dated Aug. 15, 2012, 241 pages.
Plaintiff Gore's Brief in Support of Motion for Leave to Amend Its Complaint for Declaratory Judgment, US District Court for the District of Delaware, *W. L. Gore & Associates, Inc*, v. *EMD Millipore Corporation*, Civil Action No. 11-346-SLR-MPT, Document 76, Dated Aug. 15, 2012, Redacted—Publich Version, 23 pages.
AESSEAL Environmental Technology P04U and PO5U Single Bellows Component Seal Range, Jan. 2006, (Exhibit 4 to the Affidavit of Alexander H. Slocum, Ph.D., US District Court for the District of Massachusetts, *EMD Millipore Corporation* v. *AllPure Technologies, Inc.*, Civil Action No. 1:11-cv-10221-DPW,Document 66-4, dated May 2, 2012), 5 pages.
Purdue University—School of Mechanical Engineering—International Compressor Engineering Conference, article by J. W. Abar, "End Face Seals for Air-Conditioning Compressors", 1972 (Exhibit 5 to the Affidiavit of Alexander H. Solcum, Ph.D, US District Court for the District of Massachusetts, *EMD Millipore Corporation* v. *AllPure Technologies, Inc.*, Civil Action No. 1:11-cv-10221-DPW,Document 66-5, dated May 2, 2012), 15 pages.
Memorandum and Order regarding Claim Construction, U S District Court for the District of Massachusetts, *EMD Millipore Corporation* v. *Allpure Technologies, Inc.*, Civil Action No. 11-10221-DPW, Document 81, Dated Oct. 11, 2012, 34 pages.
Photographs (7 photos) of the Millipore commercially needleless sampling device; available at least as of Feb. 14, 2012, 7 pages.
Photographs (3 photos) of the Millipore Opticap XLT base, commercially available in 2002, No earlier than Jan. 1, 2002, 3 pages.
Photographs (3 photos) of the Millipore Opticap XL 300, commercially available in 2002, No earlier than Jan. 1, 2002, 3 pages.
Brief for Plaintiff—Appellant, US Court of Appeals, Appeal Nos. 2011-1029, 2012-1371, *EMD Millipore Corporation* v. *W. L. Gore & Associates, Inc.*, Document 40, dated Jul. 25, 2012 and filed Jul. 27, 2012, 147 pages, submitted in 2 parts.
Brief of Defendant—Appellee W. L. Gore & Associates, Inc., US Court of Appeals, Appeal Nos. 2011-1029, 2012-1371, *EMD Millipore Corporation* v. *W. L. Gore & Associates, Inc.*, Document 52, filed Oct. 9, 2012, 75 pages.
Reply Brief for Plaintiff—Appellant, US Court of Appeals, Appeal Nos. 2011-1029, 2012-1371, *EMD Millipore Corporation* v. *W. L. Gore & Associates, Inc.*, Document 57, Dated Nov. 9, 2012, 42 pages.
AllPure Takeone Aseptic Sampling System Overview, 2 pgs. (Deposition Exhibit dated Nov. 12, 2012).
Amesil HG Silicone Steam Valve Aseptic Connector-Flow Control, 2 pages, Bates No. WLG00005888-WLG00005889 (WLG-DEL 00005946-WLG-DEL 00005947).
ASI Life Sciences, three 60, Single Use Aseptic Sampling System, www.asisus.com, Jan. 10, 2013, 8 pages.
Fluid Line Technology Corporation, Product Catalog, 32 pages, Bates No. FLT000003-FLT000034, on information and belief available as of about Nov. 2009.
Gore Single-Use Valve, for Steam-In-Place Applications, 4 pgs. 2009.
Gore STA-PURE Fluid Sampling System, for Single-Use Aseptic Applications, Secure Sampling for Bioprocessing Fluids, Dec. 2008, 4 pages.
Lynx ST Connectors, Millipore Data Sheet, Lit. No. 051750EN00, Rev. E, May 2008, 4 pages.
International Application No. PCT/US03/13073, filed Apr. 25, 2003, and Request for Express Abandonment of U.S. Appl. No. 10/423,131, filed Sep. 11, 2003, 56 pages.
MicropreSure Sanitary Sampling Valves, Millipore Data Sheet, Lit. No. DS1006EN00, May 2005, 4 pages.
Millipore Express SHF Hydrophilic Cartridge Filters, Data Sheet, May 16, 2013, www.millipore.com/catalogue, 2 pages.
Millipore, Hydrophilic Durapore Cartridges and Capsules User Guide, Lit. No. RF 1510EN00, Jan. 2002, 56 pages.
Millipore, Milliflex-P Sanitary Sampling Valves, Operation and Maintenance Instructions, Jul. 2006, 17 pages.
NovaSeptum sampling systems, EMD Millipore Data Sheet, Jun. 2012, Lit. # DS0050EN00, Rev. E., 10 pgs.
NovaSeptum sampling systems, Merck Millipore Data Sheet, Apr. 2013, Lit. # DS0050EN00, Rev. H., 10 pgs.
Millipore, NovaSeptum AV Sterile Sampling System, for liquid sampling, User Guide, Lit. No. 00000069TP, Rev. A., Jun. 2006, 2 pages.
Millipore Opticap XL and XLT Disposable Capsules, Millipore Corporation, Lit. No. PB1700EN00, Rev. B, Jun. 2004, 4 pages.
Pharmaceutical Engineering, vol. 23, No. 3, May/Jun. 2002, pp. 1-8, "Single-Use Disposable Filling for Sterile Pharmaceuticals", Belongia, et al.
Redacted email, dated Jun. 4, 2012, regarding Disposable Steam Connector, 2 pages.
Millipore, Series 2000, Single Sanitary Cartridge Housing, Instructions for Installation and Maintenance, Lit. No. P35265, Rev. A, Feb. 2000, 12 pages.
ThermoScientific, Data Sheet 053, Rev. 2, "Aseptic Connection Devices", 2008, 2 pages.
Miscellaneous Communication mailed Apr. 18, 2012 and Apr. 16, 2012 in co-pending U.S. Appl. No. 12/284,666.
Office Action mailed Sep. 30, 2011 in corresponding parent U.S. Appl. No. 12/638,242.
Notice of Allowance Feb. 16, 2012 in corresponding parent U.S. Appl. No. 12/638,242.
Final Rejection mailed Jun. 19, 2013 in co-pending U.S. Appl. No. 12/291,814.
Notice of Allowance mailed Jun. 21, 2013 in co-pending U.S. Appl. No. 12/284,666.

DEVICE FOR THE TRANSFER OF A MEDIUM

This application is a divisional of U.S. patent application Ser. No. 12/638,242 filed Dec. 15, 2009, the disclosure of which is incorporated herein by reference, and claims priority of French patent application No. 0858804 filed on Dec. 18, 2008.

The present invention concerns the transfer of media, such as liquids, into or from a container.

It is especially important, in particular in the field of pharmaceutics and biotechnologies to be able to take off samples to analyze them, for example to perform microbiological verifications in culture tanks, for counting cells, for chemical analysis, etc.

Such taking off must be performed while minimizing as much as possible the risks of contamination of the taken-off sample and of the medium from which the sample is taken off.

Devices are already known, in particular from European patent EP 0 858 589, for the transfer of a medium into or from a container comprising a substantially cylindrical magazine as well as several transfer elements for transfer of the medium, each disposed in a cavity of the magazine, each cavity issuing on the same face of the magazine which is adapted to cooperate with a wall of the container.

Each transfer element comprises a transfer duct provided at one end with a needle, a septum having a portion adapted to seal with the container and to be pierced by the point of the needle, and a needle driving device adapted to pass that needle from a waiting position in which it is situated within the cavity and isolated from the interior of the container by the septum to a working position in which its point projects from the cavity by the portion of the septum that is adapted to be pierced.

The transfer duct of each transfer element may be connected, at the opposite end from the needle, to a take-off bag to collect the sample coming from the container after it has passed through the transfer element.

The duct also has a bent portion which is accommodated in a window of the magazine body to keep the transfer element locked in its waiting position in order to prevent any risk of having the septum perforated by the needle inadvertently (for example due to incorrect manipulation by the operator).

To unlock that transfer member, the operator makes the duct of that element rotate to free its bent portion from the window and place that portion along the axis of a groove formed in the body of the magazine and along which, by pressing on the driving unit towards the container, the duct is adapted to slide to cause the needle to pass from its waiting position to its working position in order to allow the transfer of the fluid into or from the container.

The invention aims to provide a device that is also adapted to enable the transfer of a medium but which at the same time is more economic, is more practical, and gives better performance To that end it provides a device for the transfer of a medium into or from a container comprising a magazine and at least one transfer element for transfer of said medium received in a cavity formed in said magazine, said transfer element comprising a transfer duct for transfer of said medium provided at one end with a needle, a septum having a portion adapted to seal with the container and to be pierced by the point of said needle, and a unit for driving said needle adapted to make said needle pass from a waiting position in which its point is situated within said cavity to a working position in which its point projects from said cavity through said portion of the septum that is adapted to be pierced, said transfer element also comprising locking means adapted to cooperate with complementary locking means of said magazine to lock said needle in its waiting position; characterized in that said locking means belong to said driving unit and cooperate with said complementary locking means at a location of the magazine that is distinct from the location through which, at the opposite end from the needle, said duct issues from the cavity.

In the device according to the invention, the locking function is no longer provided by a portion of the duct but by dedicated locking means which are present on the driving unit such that it is possible to dispense with the bent portion of the duct which was necessary in the device of the prior art to provide the locking function.

The fact that dedicated locking means cooperate with complementary locking means at a location which is situated away from the location through which the transfer duct issues from the cavity (at the opposite end from the needle) makes it possible to provide a transfer duct of simpler form than that of the device of the prior art (for example of substantially rectilinear form).

The septum and the driving unit may thus, by virtue of the simple form of the transfer duct, be produced for example by overmolding around that duct so rendering the device according to the invention much easier and less costly manufacture.

The manufacture of the septum by overmolding makes that septum more resistant whether in terms of sealing or wear (caused by repeated sterilization operations of the transfer element for example).

The possibility of producing a duct of simpler form also leaves a greater possibility to choice of materials, in particular for the material which constitutes the needle (for example of polymer material).

According to features preferred for reasons of simplicity and convenience both with regard to manufacturing and with regard to use, said locking means and said complementary locking means are also adapted to lock said needle in its working position.

This makes it possible to improve the safety of use by avoiding any risk of having the needle return inadvertently to its waiting position due to the compression forces exerted by the septum against that needle.

Furthermore, this is a way for the operator, knowing that he must lock the needle in its working position, of ensuring that he has indeed perforated the septum since he is thus induced to press on the actuating unit until it has reached that locked position.

According to other preferred features, said locking means and said complementary locking means are adapted to perform the locking by latching.

The locking by latching of the transfer element to the magazine (rather than by rotation) enables a considerable space to be freed to place, in a magazine of the same diameter as in that of the prior art, more transfer elements (so increasing the number of take-off points from the container).

According to still other preferred features:
said locking means of said driving unit are moveable radially relative to said complementary locking means of said magazine;
said driving unit comprises a body fixed to said needle a driving key, and a flexible arm connecting said body to said key; and/or
said key and said arm belong to said locking means.

According to still other preferred features, said key is radially offset relative to said duct.

The presence of a driving key which is offset radially relative to the duct enables a key of greater dimensions to be produced without it preventing the movement of the needle as far as its working position which makes it easier to drive the needle and pierce the septum thereby.

More particularly, to perforate the septum in most cases requires pressing strongly (ranging from 5 to 6 kilos), such that the presence of a key of large dimensions provides comfortable manipulation for the user to perforate the septum and bring the needle to its working position.

According to still other preferred features:

said magazine comprises a body and a rib, said rib belonging to said complementary locking means and projecting laterally from said body with, in said waiting position, a portion of said key being situated facing an edge of said rib;

in said working position, said portion of said key is situated facing another edge of said rib;

the portion of said duct situated in said cavity is substantially rectilinear;

said septum comprises, in addition to said portion adapted to be pierced, a sleeve surrounding said needle at least partially and having a portion adapted to deform like bellows on passage of said needle from its waiting position to its working position.

said transfer element is obtained by molding said needle, said septum and said driving unit and/or the duct of said transfer element is adapted to be connected, at the opposite end from said needle, to a series of bags disposed one after the other and of which the reservoirs communicate with each other, whereby they are adapted to be filled one after the other on transfer of said medium through said duct.

The features and advantages of the invention will appear from the following description, given by way of preferred but non-limiting example, with reference to the accompanying drawings in which.

The transfer device 1 illustrated in FIGS. 1 to 7 comprises a magazine 2 as well as five transfer elements 3.

Figure 1:
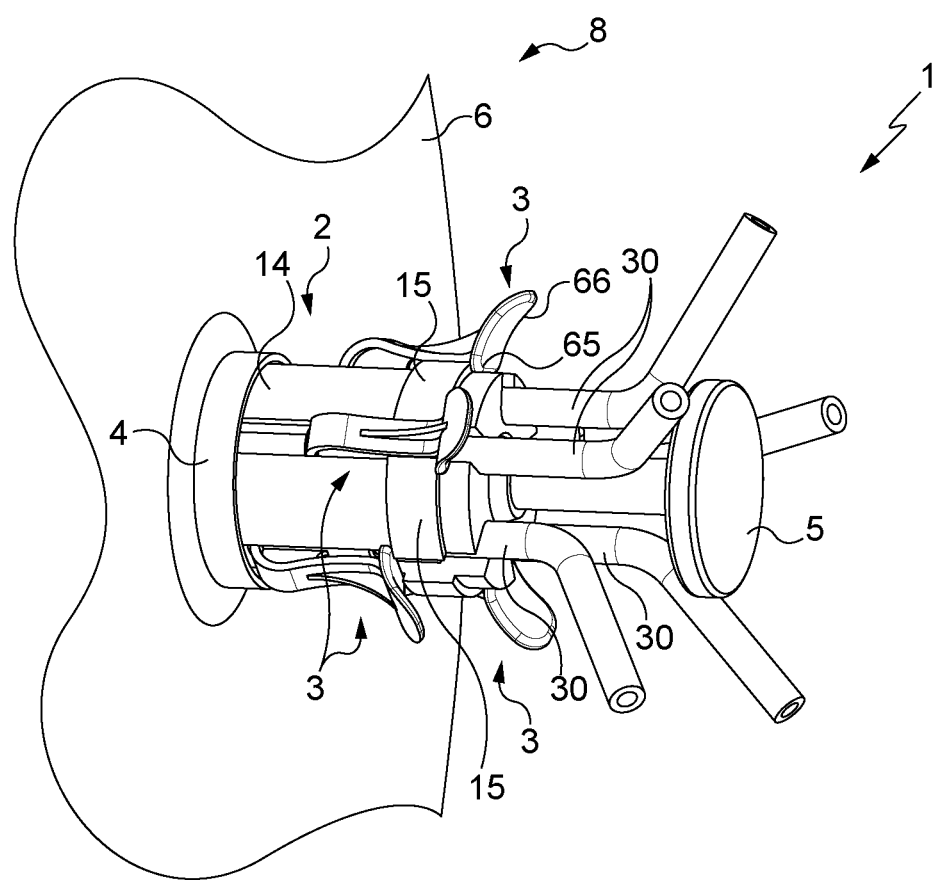
FIG. 1 is a perspective view of a device according to the invention fixed to the wall of a container with one of the transfer elements of that device being represented in its working position to enable the transfer of the liquid whereas the other transfer elements are represented in their waiting position.
Figure 2:
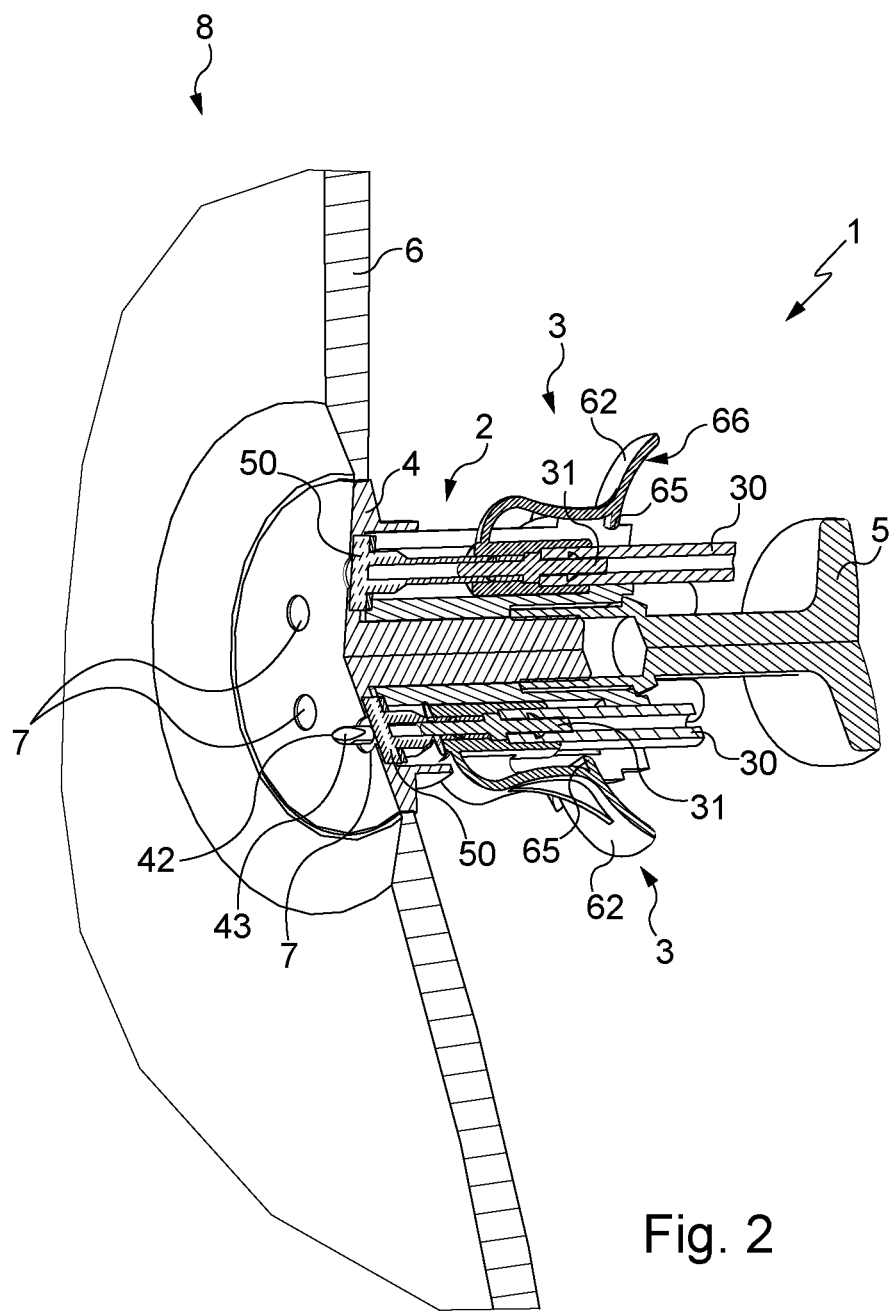
FIG. 2 is a similar view to FIG. 1 but from a different angle and shown cut away in order to illustrate the inside of the device.
Figure 3:
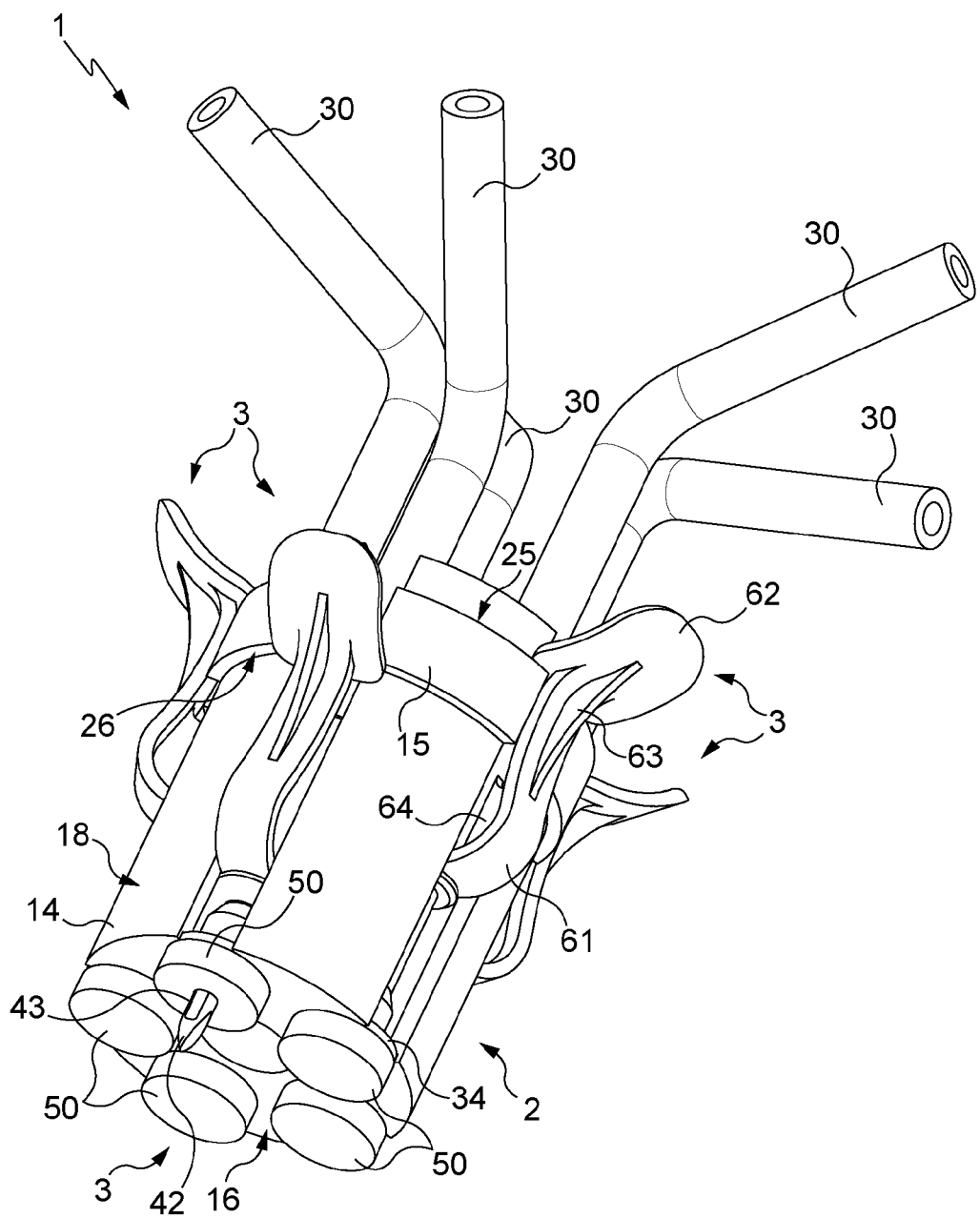
FIG. 3 is a perspective view presenting the device in isolation.

As illustrated in FIG. 1, the assembly formed by the magazine 2 and the five transfer elements 3 is to be joined to a coupling 4 which is fixed to a wall 6 of the container 8 in which five openings 7 are formed to enable the end portions of the transfer elements 3 to enter inside the container.

A tightening handle 5 to screw onto the coupling 4 enables the device to be pressed against that coupling to make the sealing connection to the container.

The magazine 2 of the transfer device is of cylindrical general form and has a body 14 and a rib 15 formed from five segments.

The body 14 has two main faces 16 and 17 and a lateral face 18 connecting said main faces together. A tubular central cavity 19 and five cavities 20 surrounding that central cavity 19 are formed in the body.

In each of the cavities 20 a transfer element 3 is received, those cavities issuing at the faces 16 and 17 as well as at the face 18 to form a slide track in which the transfer element accommodated therein is adapted to slide.

At the end of each cavity 20 an annular groove 21 is formed in the body 14.

The central cavity 19 also issues at the faces 16 and 17 and has three tubular portions 22, 23, 24 allowing the passage of a shaft of the handle 5 of which the end is threaded to be screwed to the coupling 4.

The rib 15 of the magazine is interrupted at each cavity 20 and thus has five segments situated in the neighborhood of face 17 and extending from an edge of one cavity 20 to the neighboring cavity.

A transfer unit 3 is described next with reference to FIGS. 1 to 9.

Each transfer unit 3 comprises a tube 30, a needle 31, a septum 32, a driving unit 33 for driving the needle 31 and a washer 34.

The needle 31 has a central portion 35, and on respective opposite sides of that portion, an end portion 36 and an end portion 37 delimiting a channel 38 within that needle.

Portion 36 is engaged in the tube 30 and is provided with a set of teeth 39 to hold that portion to the tube 30. That portion 36 issues by an opening 40 into tube 30.

Portion 37 is engaged in the septum 32 and is provided with a set of teeth 41 to hold that portion to the septum 32.

That portion 37 has a point 42 provided to perforate the septum on movement of the needle and a lateral opening 43 giving access to the channel 38.

The tube 30 delimits a channel 29 communicating with the channel 38 by the opening 40, the needle 31 and the tube 30 together forming a duct 45 for transfer of the liquid from the container to, for example, a series of bags to fill. That duct 45 is substantially rectilinear over the whole of the length of the section that is received in the cavity 20.

Tube 30 issues from cavity 20 at the opposite face 17 from face 16 and continues with a tubular portion which connects to a take-off bag.

The septum 32 is of silicone and comprises a solid portion in the form of a disc 50, a first tubular portion 51, a second tubular portion 52 and a frusto-conical portion 53.

The frusto-conical portion 53 is situated between the tubular portions 51 and 52 while tubular portion 51 is situated between disc 50 and frusto-conical portion 53.

The inner diameters of portions 51 and 52 are equal while the outer diameter of portion 51 is greater than that of portion 52, that portion thus being of greater thickness than that of portion 52.

Tubular portion 51 joins to disc 50 while being centered relative thereto.

Portions 51 to 53 thus form a sleeve in which portion 37 of the needle is received, with the edge of portion 52 abutting the edge of the central portion 35 of that needle.

The disc-shaped portion 50 is the portion of the septum which is pressed at a corresponding opening 7 (FIG. 1) against the wall 6 of the container when the handle 5 is screwed to the coupling 4 in order to provide the sealing obturation of that opening until that portion 50 is perforated by the needle 31.

The washer 34 surrounds the tubular portion 51 and is accommodated, when the transfer element is placed in a cavity 20 of the magazine in an annular groove 21 matching that washer 34 and the disc 50 which are against each other.

The washer is of material which is strong and stiff in order to provide the homogeneous compression of the disc 50 against the wall 6 of the container 8 in order to ensure the sealing connection of the magazine to that container.

The driving unit 33 comprises a tubular body 60, a flexible arm 61 and a driving key 62.

The body 60 is connected to the key 62 via the flexible arm 61.

The body 60 partially surrounds portion 52 of the septum and thus portion 37 of the needle, entirely surrounds the central tubular portion 35 and also partially surrounds portion 38.

This driving unit 33 also has a reinforcing rib 63 between the key 62 and the arm 61 as well as a reinforcing rib 64 between the arm 61 and the body 60 (FIG. 6) so as to ensure sufficient mechanical strength when the operator acts on that unit.

The driving unit 33, the septum 32 and the duct 45 are produced by molding those members onto each other.

The arm 61 and the key 62 form locking means adapted to cooperate with a corresponding segment of rib 15 such that this cooperation takes place at a location of the magazine 2 which is distinct from the location by which the duct 45 issues from the cavity 20, at the opposite end from the needle 31 (on face 17 of the magazine).

The assembly of a transfer element 3 in the magazine 2 is carried out by inserting that element in the cavity 20 from the side where the opening of that cavity is, which is situated on face 16, then by sliding that element in the direction going from face 16 towards face 17.

The portion 65 of the key 62 thus comes into abutment with the edge 26 of rib 15 driving the radial displacement of the key 62 by elastic deformation of the arm 61, the portion 65 of that key thus moving away from the edge 26 to pass over that rib until it has gone past it and to arrive, by elastic return of the arm 61, on the same side as, and facing, the opposite edge 25 of that rib to the edge 26.

Figure 4:
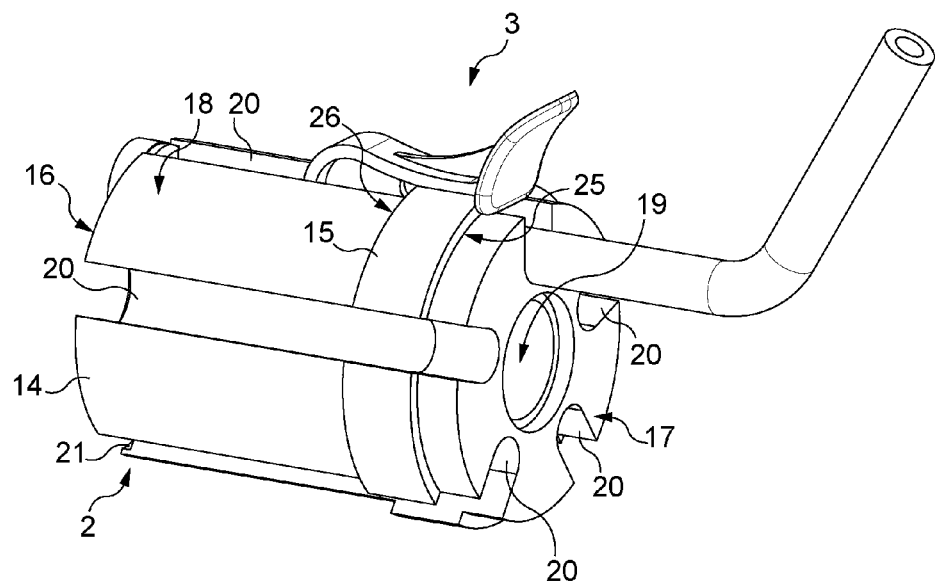
FIGS. 4 and 5 are respectively a perspective view and a section view in elevation taken on a median plane of symmetry of the device in which only one of the transfer elements is represented disposed in its waiting position.
Figure 5:
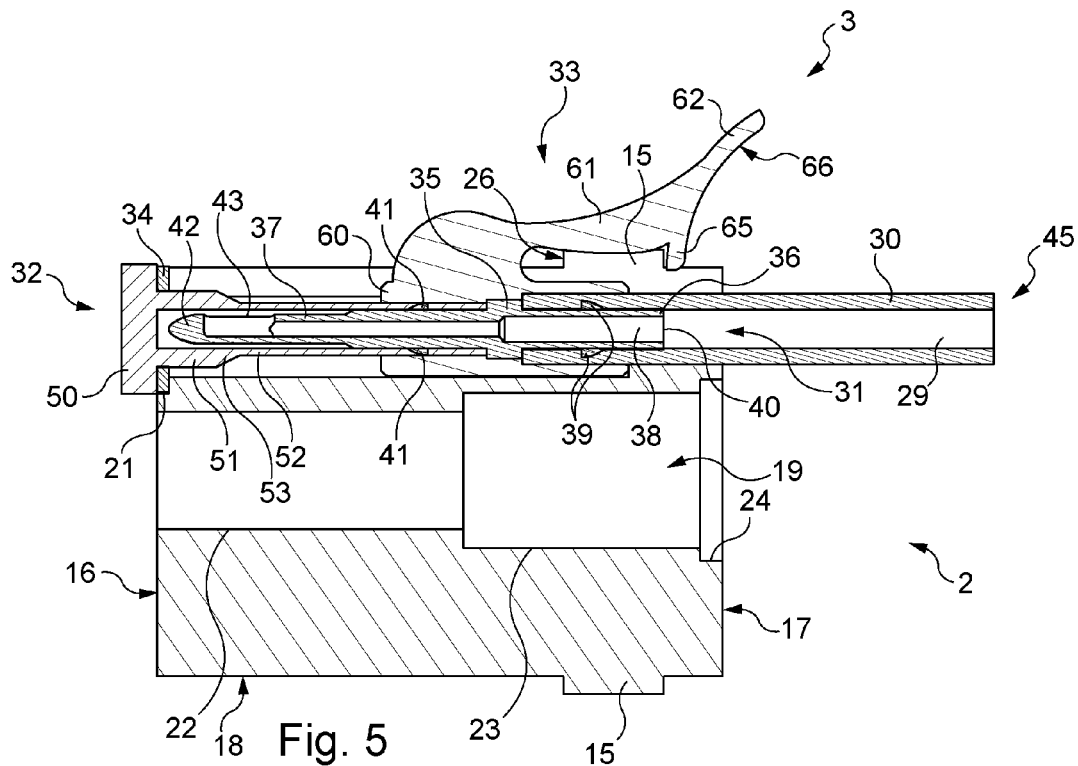

In that waiting position illustrated in FIGS. 4 and 5, the transfer element 3 is thus locked by latching of the magazine within the cavity 20, the washer 34 is engaged in the annular groove 21 and only portion 50 of the disc projects from face 16 of the magazine 2. The needle 31 is entirely accommodated in the cavity 20 with the portion 37 of the needle being entirely situated within the sleeve delimited by the tubular portions 51, 52 and 53 of the septum.

Figure 6:
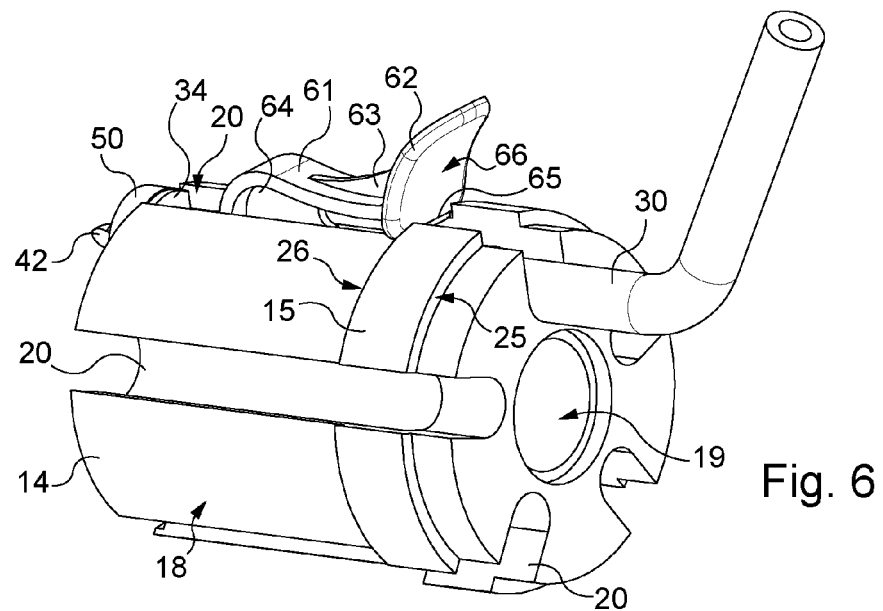
FIGS. 6 and 7 are similar views to FIGS. 4 and 5 and represent that transfer element in its working position.
Figure 7:
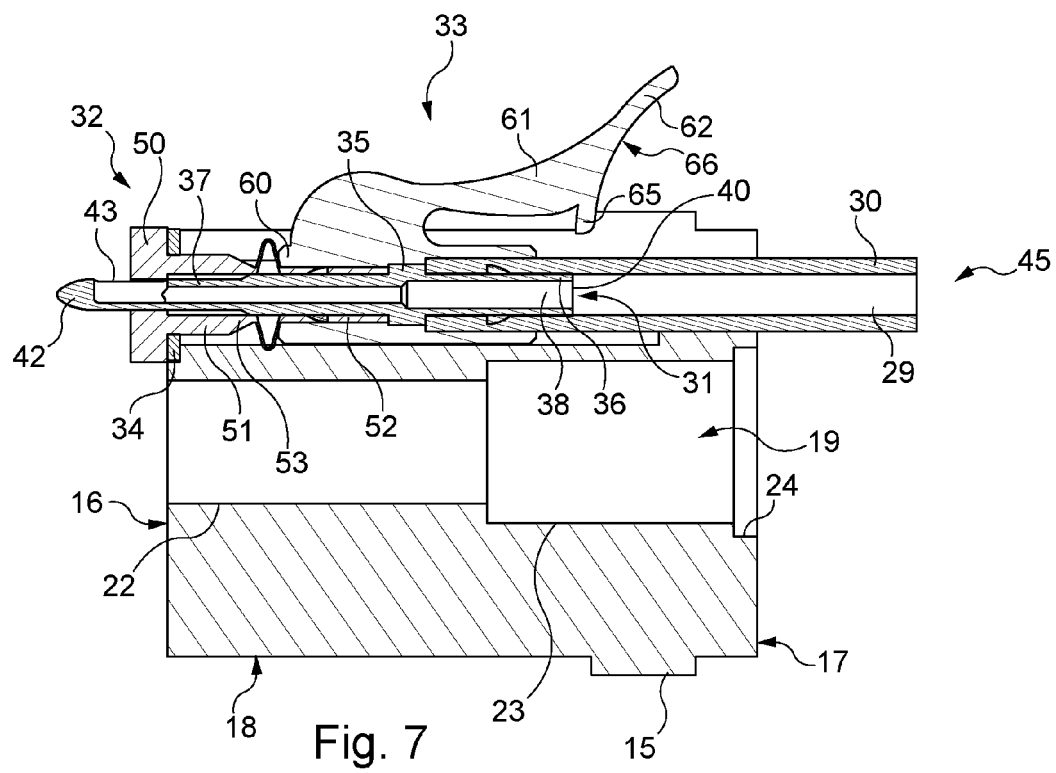
Figure 8:
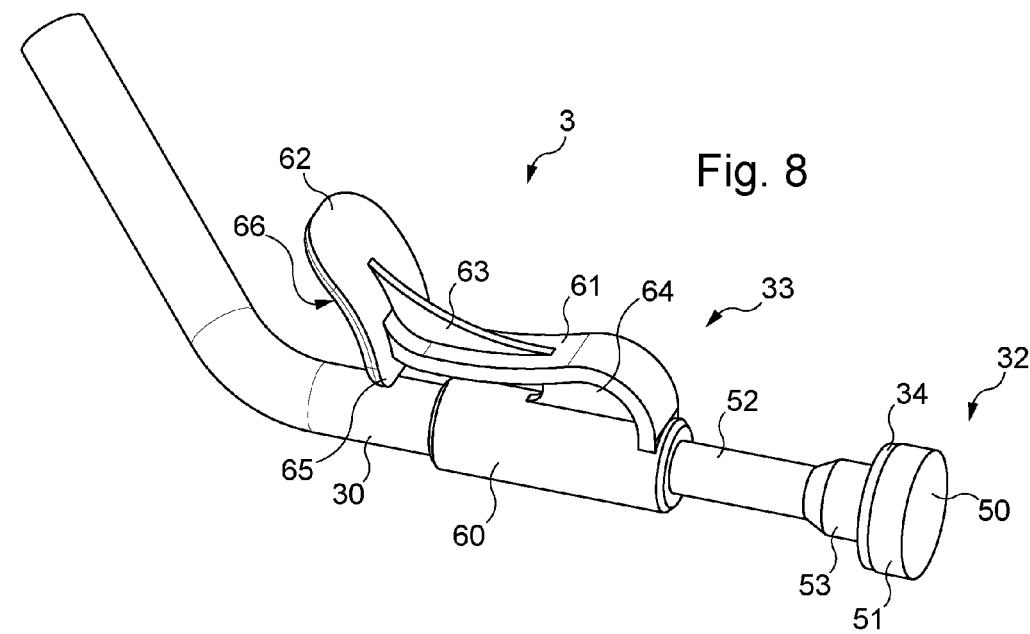
FIG. 8 is a perspective view illustrating that transfer element in isolation with the conformation that it assumes when it is in its waiting position.
Figure 9:
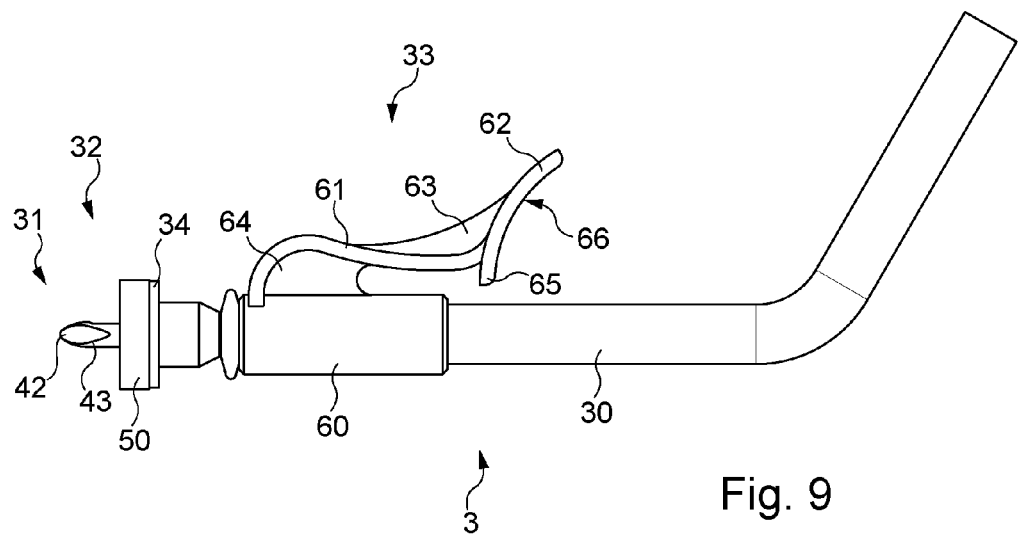
FIG. 9 is a view in elevation illustrating that transfer element in the conformation it assumes when it is in that working position.

Once the transfer element has been thus assembled, the driving unit makes it possible to pass the needle 31 of that element from its waiting position to a working position permitting the transfer of the liquid which is illustrated in FIGS. 6 and 7.

In this working position of the transfer element 3, the point 42 and a part of the opening 43 of the portion 37 of the needle project from the disc 50 such that the part of the opening 43 which projects from that disc communicates with the inside of the container.

In this position, the part of the tubular portion 52 of the septum 32 which is not covered by the tubular body 60 of the unit 33 is folded bellows-fashion between the body 60 and the tubular portion 51.

In this position, part 65 of the key 62 is again situated facing and against the edge 26 of the rib 15, pressed against that rib by the deformed septum 32, such that the needle is held locked by latching in its working position.

To pass from the waiting position to the working position, the operator lifts the key 62 by pressing on its face 66 so as to deform the flexible arm 61 to radially separate portion 65 of that key from the edge 25 of the corresponding segment of the rib 15 of the magazine. The operator also presses on that face 66 towards the container 8 to drive the movement of the driving unit 33 and with it the needle 31. During the movement of the needle 31 the point 42 of that needle comes to press on then perforate at its center the silicone disc 50 of the septum.

The operator continues that movement until the needle reaches its working position and then releases the key such that the portion 65 of that key comes into place facing the edge 26 of the rib 15 by elastic return of the arm 6.

The radial offsetting of the key 66 relative to the needle 31 by virtue of the arm 61 enables the key to have dimensions enabling it to be manipulated in good conditions and in particular in order to perforate the septum without having to exert too much effort by virtue of the large contact surface 66 of that key.

When the needle is thus placed in its working position, it is possible to make the liquid pass from the container to attain one or more bags connected to the opposite end of the tube 30 to the needle 31.

Conversely and to once again isolate those bags from the container, it is also possible to pass back the needle from its working position to its waiting position, the material of the disc 50, here silicone, having sufficient elastic properties to enable it to sealingly close on itself again after the withdrawal of the needle even though it has been perforated.

The needle 31 and the tube 30 are thus once again isolated from the inside of the container so preventing the liquid contained by that container from flowing via that needle which avoids any risk of contamination by germs which could get back to the container via the transfer element 3 if it were not brought back to its waiting position.

A description will now be given with the aid of FIG. 10 of an arrangement of bags to connect to a transfer element 3 to take off a liquid.

This arrangement 70 has a plurality of bags 71 disposed in series. Each bag is formed from two thermoplastics sheets sealed to each other by a weld bead 72 delimiting a reservoir 73. The bags are connected to each other by detachable borders 76 and 77. Each bag has an end piece 74 (here a section of tube) provided to enable the filling of the corresponding reservoir 73 and an end piece 75 (also a section of tube) connected to the end piece 74 of the following neighboring bag (and formed from a single piece with it in the illustrated example) to enable the passage of the liquid from one bag to the other. The end piece 74 of the first bag of the series of bags 70 is connected to the tube 30 of a transfer element 3 whereas a plug 83 is engaged in the end piece 75 of the last bag.

The transfer element 3 is also packaged in a bag (not illustrated) within which it is disposed to avoid any risk of contamination while it is not used, the element 3 only being extracted from that bag just before being installed in a cavity 20 of a magazine 2.

Each bag also has, at the opposite end to the location of the end pieces 74 and 75, an end piece 78 for draining the reservoir 73 of which one end issues into the reservoir 73 and of which the other end issues into a space 79 situated between the two thermoplastics sheets which is closed but not welded.

At the edge of the bags that is adjacent the end pieces 74 and 75 there is also fixed to those bags an extruded profile member 80 adapted to be received in a channel member 81 so as to hold those bags horizontal, those channel members 81 having at their end an elbow portion received in a receiving receptacle 82.

When the transfer element 3 is engaged in its working position, the liquid coming from the container passes through the needle 31 then the tube 30 to enter by the end piece 74 of the first bag into the reservoir 73 of that bag. That reservoir 73 fills and the liquid, once that reservoir has been filled, continues to flow through the second reservoir by flowing via end piece 75 of the preceding bag and so forth until it reaches the last bag 71.

The operator stops the flow of the liquid (by passing the transfer element back from its working position to its waiting position) as soon as he observes that the liquid occupies the reservoir 73 of the last bag 71 of the series of bags, so indicating to him that all the previous bags are already full of liquid and free of air.

The flow of the liquid is stopped before that last bag is entirely filled in order to avoid any risk of bursting, that last bag being used as an indicator of the filling of the preceding bags.

It is then possible to retrieve the bags one by one through use of a tool (not illustrated) adapted to obturate the end pieces 74 and 75 by heating them.

The content of each bag may then be taken off by separating the two thermoplastics sheets from each other to clear the access to the space 79 and to the take-off end piece 78 in order to connect to that end piece a take take-off device such as a syringe.

Figure 11:
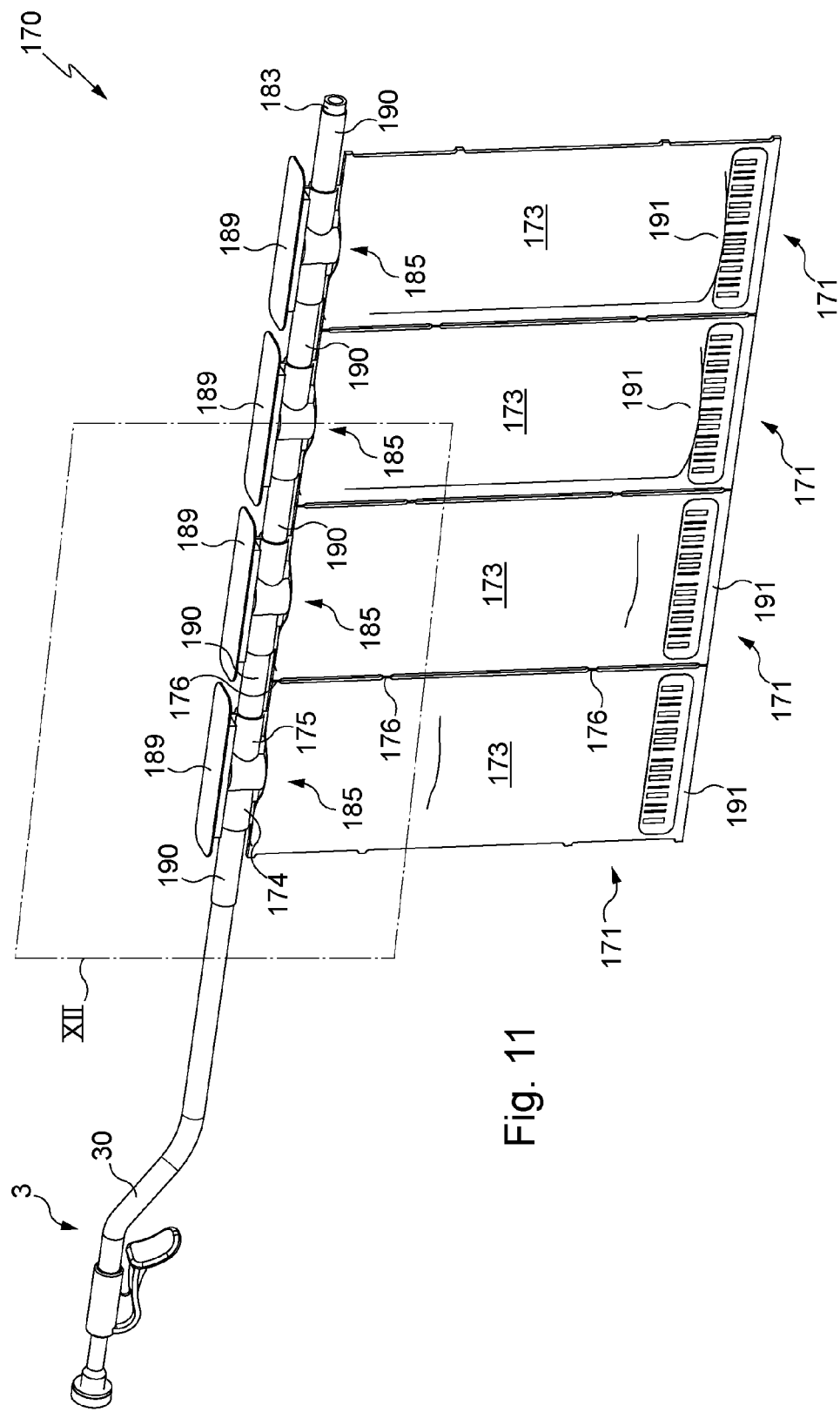
FIG. 11 is a similar view to FIG. 10 but for bags having a different conformation.
Figure 12:
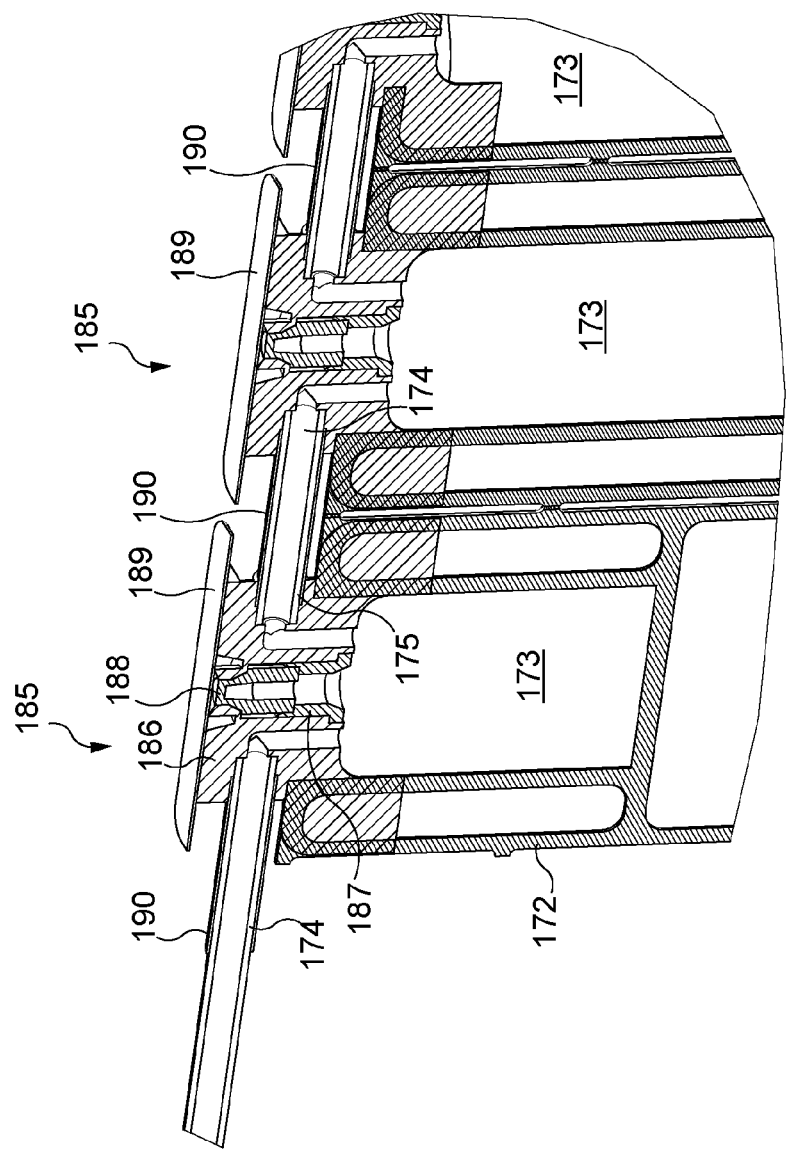
FIG. 12 is an enlarged view of the detail identified by XII in FIG. 11, shown cut away.
Figure 13:
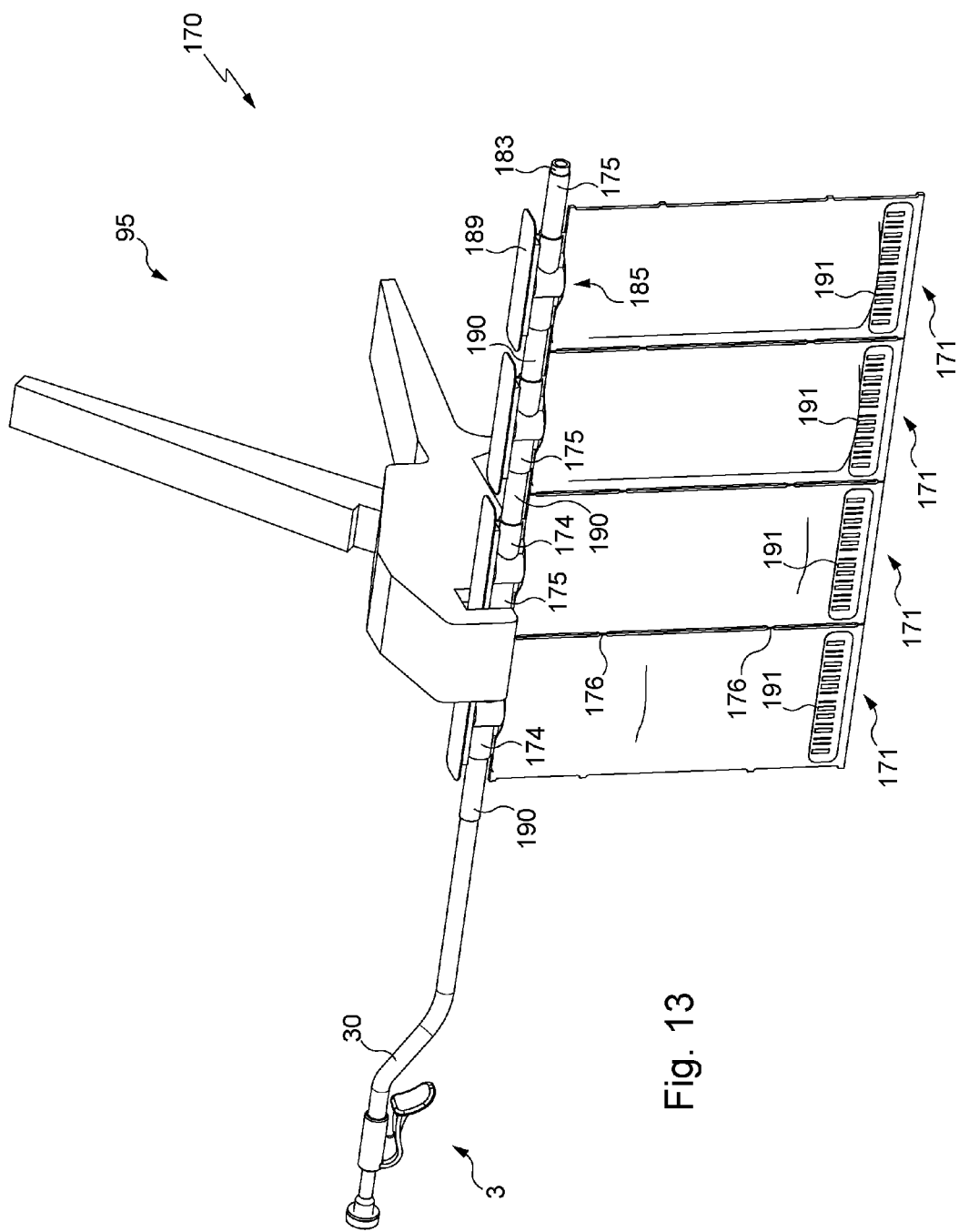
FIG. 13 is a similar view to FIG. 11 but on which crimping pliers are also represented which are provided to detach the bags from each other.

Another arrangement of the bags is illustrated in FIGS. 11 to 13.

Generally speaking, the same reference numbers increased by 100 are used for similar elements.

The arrangement 170 illustrated in these Figures is formed by a plurality of bags 171 disposed one after the other in order for them to fill successively.

Each bag 171 is provided with a perforable valve 185.

This valve has a first body 186, a second body 187 as well as a perforable septum of silicone 188 to enable the take-off of the liquid once the bag has been filled.

The septum 188 is compressed between the body 186 and 187, with the faces of the body 186 and of the septum 188 that are turned outwardly of the bag being covered by a peelable protective film 189. A metal tube 190 partially surrounds each pair of end pieces 174 and 175 (which are formed as a single piece in the illustrated example) as well as the end piece 174 which is connected to the tube 30.

A bar code 191 for identification is also present on each bag.

The bags are detached from each other using a crimping pliers 95 illustrated in FIG. 13 that are provided for severing them by crushing the tubes 190 so as to provide the sealing disconnection of the bags from each other by compression of the end pieces 174 and 175.

Figure 10:
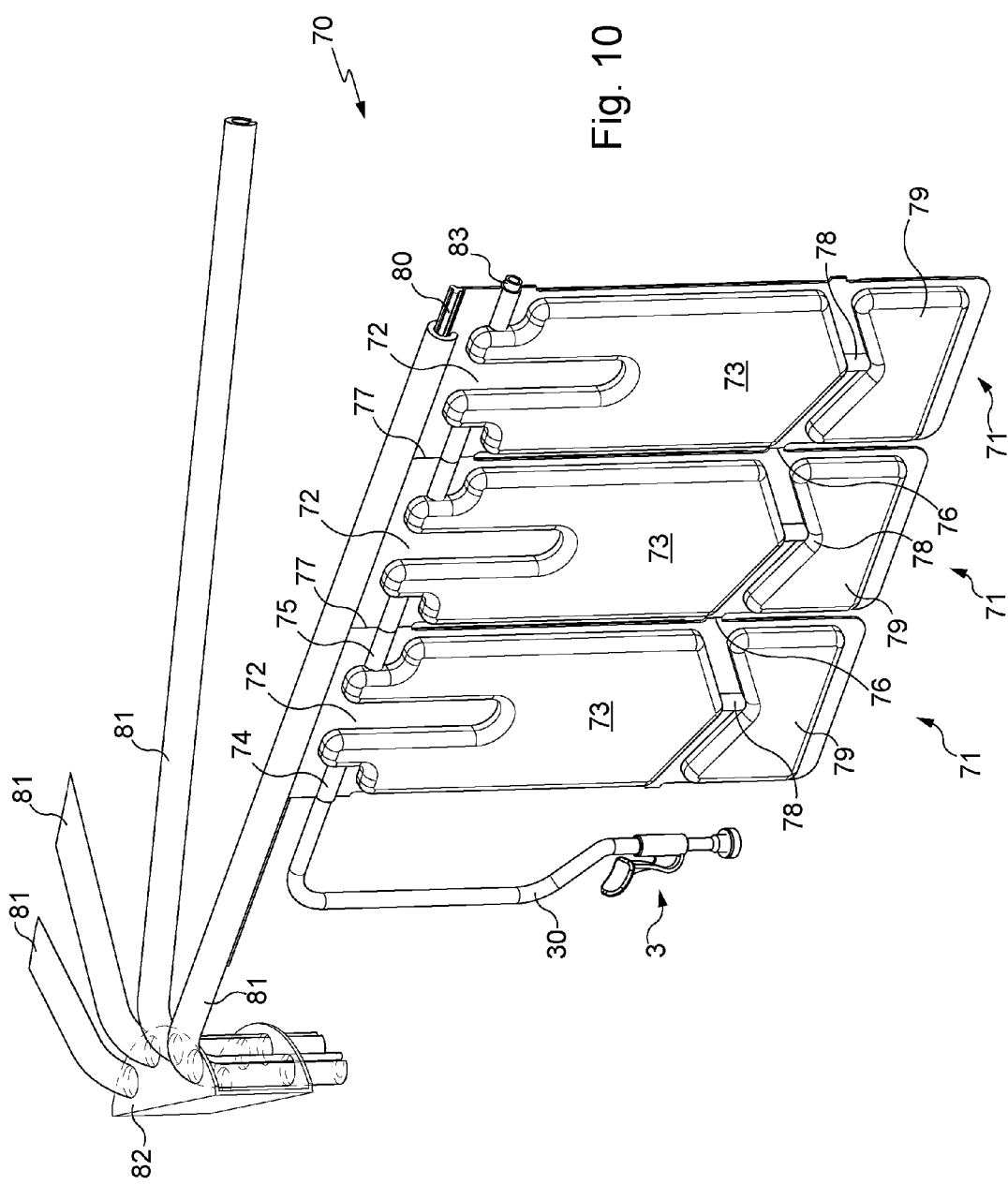
FIG. 10 is a perspective view illustrating that transfer element connected to a series of take-off bags.

The bags may all have a reservoir of the same capacity as for the embodiment illustrated in FIG. 10 or capacities variable from one bag to the other as for the embodiment illustrated in FIGS. 11 to 13, depending on the conformation of the weld bead of each bag.

As a variant the locking means of the driving unit are only adapted to provide locking in the waiting position and/or those locking means are not latching means but any other type of locking means.

In another variant the medium to transfer is not a liquid but for example a gas to take off to analyze or any other type of fluid medium.

It is also to be noted that the device according to the invention makes it possible to perform the transfer of a medium not necessarily from the container to the bags but also, for example, from a bag pre-filled with medium to a container.

The device according to the invention is also intended for transferring a medium into or from any type of container other than a tank, such as containers with flexible walls such as a bag or a pipe, a connector being mounted on those containers adapted to cooperate with a magazine.

The present invention is not limited to the embodiments described and represented, but encompasses any variant form thereof.

The invention claimed is:

1. A method of transferring a medium into or from a container, comprising:
   providing a transfer device comprising:
      a magazine,
      at least one transfer element for transferring a medium into or from a container through a cavity in the magazine, the transfer element comprising:
         a transfer duct comprising a needle at one end for transferring the medium;
         a septum for sealing the container and being pierceable by the needle, and;
         a driving unit for moving the needle from a waiting position in which its point is situated within the cavity to a working position in which its point projects from the cavity through a portion of the septum and extends into the container to enable transfer of the medium; and
         a locking mechanism for locking said transfer duct and said needle in said waiting position;
   actuating said locking mechanism so that said needle is movable to said working position;
   driving said needle with said driving unit from said waiting position to said working position; and
   passing said medium from said transfer duct to said container or from said container to said transfer duct through said needle.

2. The method of claim 1, further comprising actuating said locking mechanism to lock said needle in said working position.

3. The method of claim 2, further comprising unlocking said needle from said working position by further actuating said locking mechanism, driving said needle back to said waiting position with said drive unit, and re-locking said needle in said waiting position.

4. A method of transferring fluid to a bag, comprising:
   providing a bag in fluid communication with a transfer device, said transfer device comprising:
      a magazine,
      at least one transfer element for transferring fluid into or from said bag, the transfer element comprising:
         a transfer duct comprising a needle at one end for transferring the fluid;
         a septum pierceable by the needle, and;

a driving unit for moving the needle from a waiting position in which its point is situated within the cavity to a working position in which its point projects from the cavity through a portion of the septum to enable transfer of the fluid; and a locking mechanism for locking said transfer duct and said needle in said waiting position;

providing a source of fluid;

actuating said locking mechanism so that said needle is movable to said working position;

driving said needle with said driving unit from said waiting position to said working position, thereby penetrating said septum; and passing said fluid from said transfer duct to said bag through said needle.

5. The method of claim 4, further comprising actuating said locking mechanism to lock said needle in said working position.

6. The method of claim 5, further comprising unlocking said needle from said working position by further actuating said locking mechanism, driving said needle back to said waiting position with said drive unit, and re-locking said needle in said waiting position.

7. The method of claim 4, further comprising a plurality of bags positioned in series.

\* \* \* \* \*